(12) United States Patent
Bengtsson et al.

(10) Patent No.: US 12,299,890 B2
(45) Date of Patent: May 13, 2025

(54) AUTOMATED TUMOR IDENTIFICATION AND SEGMENTATION WITH MEDICAL IMAGES

(71) Applicant: Genentech, Inc., South San Francisco, CA (US)

(72) Inventors: Nils Gustav Thomas Bengtsson, South San Francisco, CA (US); Richard Alan Duray Carano, South San Francisco, CA (US); Alexander James Stephen Champion De Crespigny, South San Francisco, CA (US); Jill Osborn Fredrickson, South San Francisco, CA (US); Mohamed Skander Jemaa, South San Francisco, CA (US)

(73) Assignee: GENENTECH, INC., South San Francisco, CA (US)

( * ) Notice: Subject to any disclaimer, the term of this patent is extended or adjusted under 35 U.S.C. 154(b) by 365 days.

(21) Appl. No.: 17/842,542

(22) Filed: Jun. 16, 2022

(65) Prior Publication Data

US 2022/0319008 A1 Oct. 6, 2022

Related U.S. Application Data

(63) Continuation of application No. PCT/US2020/057542, filed on Oct. 27, 2020.
(Continued)

(51) Int. Cl.
*G06T 7/00* (2017.01)
*A61B 5/00* (2006.01)
(Continued)

(52) U.S. Cl.
CPC .......... *G06T 7/0016* (2013.01); *A61B 5/4848* (2013.01); *G06T 7/12* (2017.01);
(Continued)

(58) Field of Classification Search
CPC .......... G06T 7/0016; G06T 7/12; G06T 7/62; G06T 7/70; G06T 2207/10081;
(Continued)

(56) References Cited

U.S. PATENT DOCUMENTS 10,679,352 B2 * 6/2020 Wu ........................ G06T 5/40
2019/0188870 A1 * 6/2019 Park ..................... G06T 7/0012
(Continued)

FOREIGN PATENT DOCUMENTS

CN 110223287 * 9/2019 .......... A61B 8/0825
JP 2012165910 A 9/2012
(Continued)

OTHER PUBLICATIONS

Lin, et al., Focal Loss for Dense Object Detection, arXiv: 1708.02002v2 [cs.CV], Feb. 7, 2018, 10 pages.
(Continued)

*Primary Examiner* — Jerome Grant, II
(74) *Attorney, Agent, or Firm* — Kilpatrick Townsend & Stockton LLP

(57) ABSTRACT

Medical image(s) are input into a detection network to generate mask(s) identifying a set of regions within the medical image(s), where the detection network predicts that each region identified in the mask(s) includes a depiction of a tumor of one or more tumors within the subject. For each region, the region of the medical image(s) is processed using a tumor segmentation network to generate one or more tumor segmentation boundaries for the tumor present within the subject. For each tumor and by using a plurality of organ-specific segmentation networks, an organ is determined within which at least part of the tumor is located. An output is generated based on the one or more tumor segmentation boundaries and locations of the organs within which at least part of the one or more tumors are located.

20 Claims, 25 Drawing Sheets

Related U.S. Application Data

(60) Provisional application No. 62/952,008, filed on Dec. 20, 2019, provisional application No. 62/990,348, filed on Mar. 16, 2020.

(51) Int. Cl.
  *G06T 7/12* (2017.01)
  *G06T 7/62* (2017.01)
  *G06T 7/70* (2017.01)

(52) U.S. Cl.
  CPC .................. *G06T 7/62* (2017.01); *G06T 7/70* (2017.01); *G06T 2207/10081* (2013.01); *G06T 2207/10088* (2013.01); *G06T 2207/20021* (2013.01); *G06T 2207/20081* (2013.01); *G06T 2207/20084* (2013.01); *G06T 2207/30096* (2013.01)

(58) Field of Classification Search
  CPC . G06T 2207/10088; G06T 2207/20021; G06T 2207/20081; G06T 2207/20084; G06T 2207/30096; G06T 2207/20076; G06T 7/0012; G06T 7/11; G06T 7/136; A61B 5/4848
  USPC ......................................................... 382/128
  See application file for complete search history.

(56) References Cited

U.S. PATENT DOCUMENTS

| | | | |
|---|---|---|---|
| 2019/0244347 A1 | 8/2019 | Buckler et al. | |
| 2019/0279359 A1* | 9/2019 | Madabhushi | G06V 10/763 |
| 2020/0105413 A1* | 4/2020 | Vladimirova | G16H 20/30 |

FOREIGN PATENT DOCUMENTS

| | | | | |
|---|---|---|---|---|
| RU | 2668699 | * | 10/2018 | ............... A61B 5/00 |
| WO | 2019103912 A2 | | 5/2019 | |
| WO | 2019239154 A1 | | 12/2019 | |
| WO | 2021126370 A1 | | 6/2021 | |

OTHER PUBLICATIONS

Heller, et al., The KiTS19 Challenge Data: 300 Kidney Tumor Cases with Clinical Context, CT Semantic Segmentations, and Surgical Outcomes, arXiv:1904.00445v2 [q-bio.QM] Mar. 15, 2020, 14 pages.

Simpson, et al., A Large Annotated Medical Image Dataset for the Development and Evaluation of Segmentation Algorithms, arXiv:1902.09063v1 [cs.CV] Feb. 25, 2019, 15 pages.

Carreira, et al., A. "Que Vadis, Action Recognition? A New Model and the Kinetics Dataset" In: CVPR (2017), pp. 6299-6308.

Kohl, et al., A Probabilistic U-Net for Segmentation of Ambiguous Images, Advances in Neural Information Processing Systems (NIPS 2018) pp. 6965-6975, arXiv:1806.05034v4 [vs.CV] Jan. 29, 2019, 28 pages.

Lin, et al., Feature Pyramid Networks for Object Detection, CVPR, arXiv: 1612.03144v2 [cs. CV] Apr. 19, 2017. 10 pages.

Socinski, et al., Atezolizumab for First-Line Treatment of Metastatic Nonsquamous NSCLC, The New England Journal of Medicine, 378, 2288-2301, 2018.

Yan, et al., Mulan: Multitask Universal Lesion Analysis Network for Joint Lesion Detection, Tagging, and Segmentation, In: Frangi, AF., Schnabel, J.A., Davatzikos, C., Alberola-Lopez, C., Fichtinger, G. (eds.) MICCAI 2019. LNCS, vol. 11769, 19 pages.

Liao, et al., Evaluate the malignancy of pulmonary nodules using the 3D deep leaky noisy-or network. IEEE Transactions on Neural Networks and Learning Systems, vol. 30, No. 11., Nov. 2019, pp. 3484-3495.

Eisenhauer, et al., New Response Evaluation Criteria in Solid Tumours: Revised RECIST Guideline (version 1.1). European Journal of Cancer 45(2009); pp. 228-247.

Zhao, et al., Exploring Intra- and Inter-Reader Variability in Unidimensional, Bi-dimensional, and Volumetric Measurements of Solid Tumors on CT Scans Reconstructed at Different Slice Intervals, European Journal of Radiology, 82(6), 2013, 22 pages.

Tang, et al., Semi-automatic RECIST Labeling on CT Scans with Cascaded Convolutional Neural Networks, arXiv:1806.09507v1 [cs.CV] Jun. 25, 2018, 9 pages, In: Frangi, A.F., Schnabel, J.A., Davatzikos, C., Alberola-Lopez, C., Fichtinger, G.(eds.) MICCAI 2019. LNCS, vol. 11765, pp. 194-202. Springer, Cham (2019).

Ardila, et al., End-to-End Lung Cancer Screening with Three-Dimensional Deep Learning on Low-Dose Chest Computed Tomography, Nature Medicine vol. 25, Jun. 2019, pp. 954-961.

O'Donovan, P.B.: The Radiologic Appearance of Lung Cancer, Oncology (Williston Park) 11(9), 1997, pp. 1387-1404.

O'Connor, et al., Imaging Intratumor Heterogeneity: Role in Therapy Response, Resistance, and Clinical Outcome. Clinical Cancer Research, 2015, 21(2), 249-257, doi: 10.1158/1078-0432.CCR-14-0990.

* cited by examiner

Correlation to RECIST Reads

Correlation to RECIST Reads

Comparison between Model vs. Full Reads

Comparison between Model vs. Full Reads

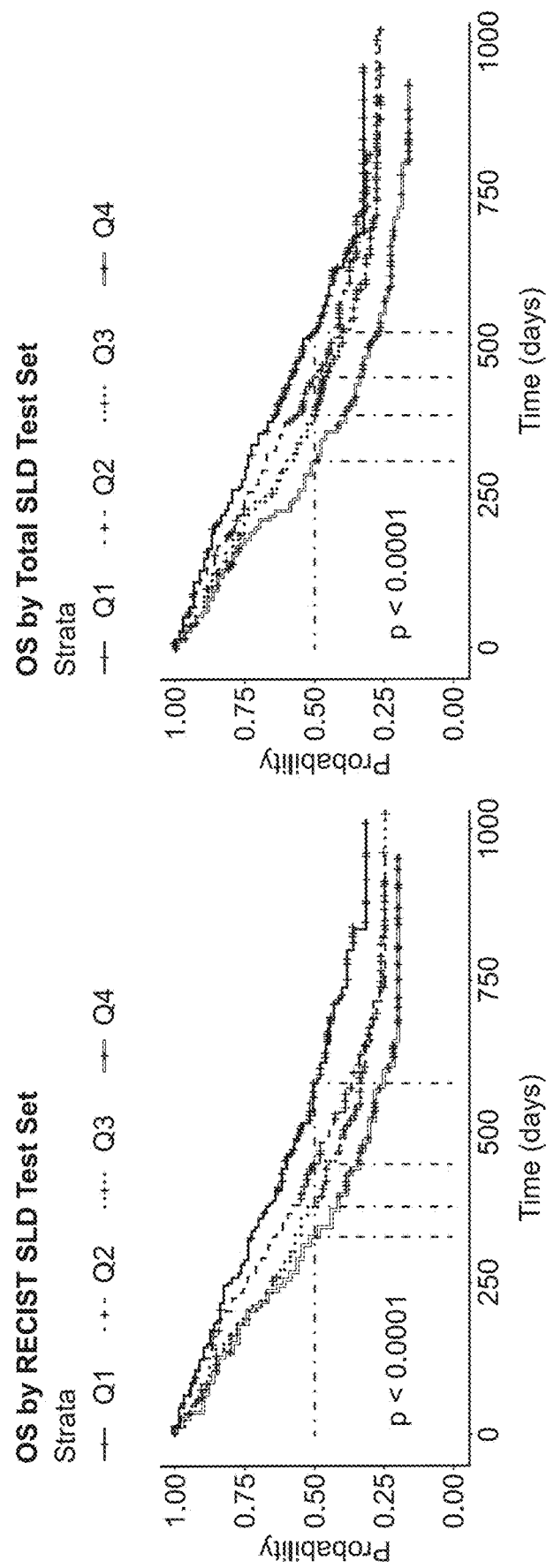

AUTOMATED TUMOR IDENTIFICATION AND SEGMENTATION WITH MEDICAL IMAGES

CROSS-REFERENCE TO RELATED APPLICATIONS

This application is a continuation of PCT/US2020/057542, filed on Oct. 27, 2020, which claims the priority to and the benefit of from U.S. Provisional Application No. 62/952,008, filed on Dec. 20, 2019 and U.S. Provisional Application No. 62/990,348, filed on Mar. 16, 2020, the entire contents of which are incorporated herein by reference for all purposes.

BACKGROUND

Medical imaging (e.g., CT scans, x-rays or MRI scans) are widely used for tumor detection in order to aide in the diagnosis and treatment of cancers (e.g., lung cancer, breast cancer, etc.). In many instances, health-care professionals assess an efficacy of a drug and/or treatment regimen through measuring changes in a tumor size or volume. Response Evaluation Criteria in Solid Tumors (RECIST) is a standardized method to assess treatment response in cancer subjects, and is a part of the regulatory standard for new oncology drug approvals. RECIST requires a substantial amount of time from a trained professional (e.g., a radiologist). Specifically, an annotator is to manually (e.g., by a radiologist) identify up to five target lesions and up to 10 non-target lesions. The annotator is to identify the perimeter of each target lesion in each scan where a cross-section of the target lesion is depicted, and records cross-sectional diameters for each target lesion. A quantitative metric (e.g., sum of longest diameters) is then determined for all target lesions. Non-target lesions are assessed qualitatively, indicating whether the non-target lesion is observed in the scan(s), and if there are unequivocal changes. Scans can be collected at multiple time points, and metrics for the target and non-target lesions can be determined for each time point. Changes in the metrics over a time period can then be used to assess a degree to which a disease is progressing and/or being effectively treated.

However RECIST includes several limitations. Namely, the method does not account for an entire disease "burden" since RECIST very frequently only measures a small subset (e.g., less than 5-10) of tumors for each subject. The technique is unable to precisely assess disease progression and/or a treatment efficacy for subjects with cancer that has metastasized to include a large number of lesions (e.g., more than 5 lesions), given that sizes of only up to 5 tumors are tracked. Furthermore, there is also inconsistency in the selection of target lesions due to variability of lesion selections, which causes significant intra- and inter-reader variability leading to differing assessments of tumor burden even within the same subject. For example, a different set of lesions may (e.g., inadvertently) be identified across different time points. Many tumors can additionally often have a heterogeneous appearance on CT and vary by location, size, and shape. For instance, lung lesions may be of cavitary or calcified type and bone metastases may (for example) take Lytic (destroys skeletal tissue) or Blastic (abnormal bone growth) form, where each lesion type is associated with different structural and visual appearance, such that due to the high variability in lesions, it is difficult to assess a stage of disease and/or each lesion of said lesion type without obtaining a full read. Thus, it would be advantageous to identify an automated technique that assesses tumor growth and/or metastasis using a more comprehensive data set and more objective techniques.

The present disclosure attempts to solve at least the above limitations by providing an automated method of tumor detection and measurement that is both consistent and accounts for an entire disease burden of a subject.

SUMMARY

Techniques described herein disclose a method for the identification and segmentation of biological objects using one or more medical images.

In various embodiments, a computer-implemented method is provided that includes accessing one or more medical images of a subject; inputting the one or more medical images into a detection network to generate one or more masks that identifies a set of regions within the one or more medical images, wherein the detection network predicts that each region of the set of regions identified in the one or more masks includes a depiction of a tumor of one or more tumors within the subject; processing, for each region of the set of regions, the region of the one or more medical images using a tumor segmentation network to generate one or more tumor segmentation boundaries for the tumor present within the subject; determining, for each tumor of the one or more tumors and by using a plurality of organ-specific segmentation networks, an organ within which at least part of the tumor is located; and generating an output based on the one or more tumor segmentation boundaries and locations of the organs within which at least part of the one or more tumors are located.

In some embodiments, processing the region to generate the one or more tumor segmentation boundaries includes: identifying, for each of multiple 2D medical image, a segmentation boundary of the tumor within are tumor segmentation boundary of the one or more tumor segmentation boundaries; and defining a three-dimensional segmentation boundary based on the segmentation boundaries associated with multiple 2D medical images, wherein the output includes or depicts the three-dimensional segmentation boundary.

In some embodiments, each of the one or more tumor segmentation boundaries is defined to be a segmentation perimeter of a two-dimensional cross section of the tumor depicted, wherein the output includes or depicts the one or more tumor segmentation boundaries.

In some embodiments, the computer-implemented method further comprises: determining, for each tumor of the one or more tumors and based on a tumor segmentation boundary of the one or more tumor segmentation boundaries, a spatial attribute that includes: a volume of the tumor; a length of the tumor along a particular dimension or longest dimension; and/or a cross-sectional area of the tumor; calculating, based on the spatial attributes, a subject-level tumor statistic of the one or more tumors, wherein the output includes the subject-level tumor statistic.

In some embodiments, the one or more tumors includes a plurality of tumors, wherein the spatial attribute determined for each tumor of the one or more tumors includes the length of the tumor along a longest dimension, and wherein the subject-level tumor statistic includes a sum of the lengths of the tumors.

In some embodiments, the computer-implemented method further comprises: determining a percentage or absolute difference between the subject-level tumor statistic and another tumor statistic associated with the subject, the other tumor statistic having been generated based on an analysis of one or more other medical images of the subject, each of the one or more other medical images having been collected at a benchmark time prior to a time at which the one or more medical images were collected, wherein the output includes or is based on the percentage or absolute difference.

In some embodiments, the computer-implemented method further comprises: comparing the percentage or absolute difference to each of one or more predetermined thresholds; determining an estimate of a prognosis, of a treatment response or of a disease state based on the threshold comparison, wherein the output includes the estimated prognosis, treatment response or disease state.

In some embodiments, the one or more medical images includes one or more computed tomography (CT) images.

In some embodiments, the one or more medical images include a whole-body or torso CT image.

In some embodiments, the one or more medical images includes one or more MRI images.

In some embodiments, the detection network is configured to use focal loss.

In some embodiments, the tumor segmentation network includes a modified U-Net that includes separable convolutions.

In some embodiments, each of the plurality of organ-specific segmentation networks includes a modified U-Net that includes separable convolutions.

In some embodiments, the computer-implemented method further comprises: determining, for each tumor of the one or more tumors and based on a being located within the organ, wherein the output includes the organ-specific counts.

In some embodiments, the computer-implemented method further comprises: inputting, by a user, the one or more medical images into a computer; and presenting, by the computer, a visual representation of at least one of the tumor segmentation boundaries.

In some embodiments, the computer-implemented method further comprises: capturing the one or more medical images with a CT machine.

In some embodiments, the computer-implemented method further comprises: providing, by a physician, a preliminary diagnosis of cancer presence or absence and any associated organ locations, the preliminary diagnosis having been determined based on the output.

In some embodiments, the computer-implemented method further comprises: providing, by a physician, a treatment recommendation based on the output.

In various embodiments, a computer-implemented method is provided that comprises: sending one or more medical images of a subject to a remote computer located across a computer network from a local computer, the remote computer configured to: input the one or more medical images into a detection network to generate one or more masks that identify a set of regions within the one or more medical images, wherein the detection network predicts that each region of the set of regions identified in the one or more masks includes a depiction of a tumor of one or more tumors within the subject; process, for each region of the set of regions, the region of the one or more medical images using a tumor segmentation network to generate one or more tumor segmentation boundaries for the tumor present within the subject; and determine, for each tumor of the one or more tumors and by using a plurality of organ-specific segmentation networks, an organ within which at least part of the tumor is located; and receiving a result based on the one or more tumor segmentation boundaries and locations of the organs within which at least part of the one or more tumors are located.

In some embodiments, the computer-implemented method further comprises: capturing the one or more medical images with an Mill machine or a CT machine.

In various embodiments, a computer-implemented method is provided that comprises: accessing one or more medical images of a subject; accessing a set of organ locations for a set of tumor lesions present in the one or more medical images; inputting the one or more medical images and the set of organ locations into a network associated with one of a plurality of therapeutic treatments to generate a score representing whether the subject is a good candidate for a particular therapeutic treatment relative to other therapeutic treatments; and returning the score.

In some embodiments, accessing the set of organ locations for the set of tumor lesions present in the one or more medical images comprises: inputting at least one of the one or more medical images into a detection network to generate one or more masks that identify a set of regions of the one or more medical images indicating predicted to depict one or more tumor lesions within the subject; and determining, for each tumor of the set of tumor lesions and by using a plurality of organ-specific segmentation networks, an organ within which at least part of the tumor is located.

In some embodiments, the detection network was trained taking a set of comparable pairs of subjects, comparable pairs of subjects having received the therapeutic treatment and having lived different periods of time after receiving the therapeutic treatment, the training comprising using a loss function that maximizes a difference in the score during training between the subjects of the pair.

In some embodiments, a loss function used during training comprises $L=-\exp(SB)/\exp(SB)+\exp(SA)$.

In some embodiments, each of the plurality of organ-specific segmentation networks comprises an inflated VGG 16 or an inflated ResNet18 network.

In some embodiments, each of the plurality of organ-specific segmentation networks comprises depthwise followed by pointwise convolutions.

In some embodiments, the computer-implemented method further comprises: inputting, by a user, the one or more medical images into a computer; and presenting, by the computer, a recommendation of whether the therapeutic treatment is appropriate for the subject.

In some embodiments, the computer-implemented method further comprises: capturing the one or more medical images with an MRI machine or CT machine.

In some embodiments, the method further comprises: proscribing, by a physician, the therapeutic treatment responsive to the score indicating that the therapeutic treatment would be beneficial to the subject.

In various embodiments, a computer-implemented method is provided that comprises: sending one or more medical images of a subject to a remote computer located across a computer network from a local computer, the remote computer configured to: access a set of organ locations for a set of tumor lesions present in the one or more medical images; and input the one or more medical images and the set of organ locations into a network associated with one of a plurality of therapeutic treatments to generate a score representing whether the subject is a good candidate for a particular therapeutic treatment relative to other therapeutic treatments; and receiving the score from the remote computer at the local computer.

In some embodiments, the computer-implemented method further comprises: capturing the one or more medical images with a CT machine or with an MM machine.

In some embodiments, a system is provided that includes one or more data processors and a non-transitory computer readable storage medium containing instructions which, when executed on the one or more data processors, cause the one or more data processors to perform part or all of one or more methods disclosed herein.

In some embodiments, a computer-program product is provided that is tangibly embodied in a non-transitory machine-readable storage medium and that includes instructions configured to cause one or more data processors to perform part or all of one or more methods disclosed herein.

BRIEF DESCRIPTION OF THE DRAWINGS

The present disclosure is described in conjunction with the appended figures:

FIGS. 22A-22B illustrate Kaplan-Meier curves for another exemplary test set. Panel A: SLD derived by manually assessed RECIST, split by quartiles, Panel B: SLD by automated method, split by quartiles.

Figure 1A:
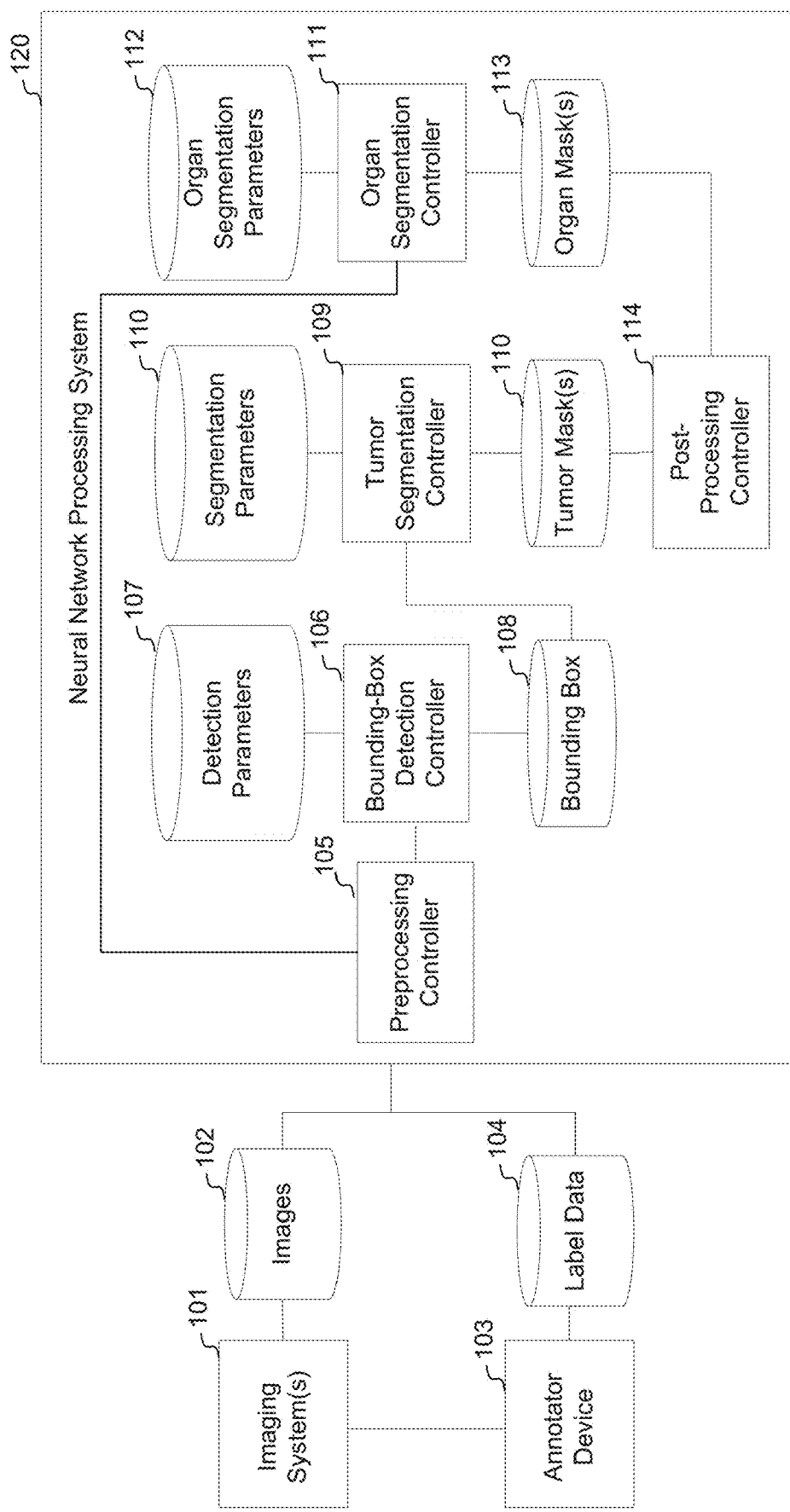
FIG. 1A illustrates an exemplary interaction system for using, collecting, and processing medical images using a multi-stage neural-network platform.

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

I. Overview

Recent image analysis efforts have focused on developing automated algorithms that can aid the radiologist's workflow by performing tumor detection and segmentation. Recent methods focus on detecting and/or segmenting RECIST lesions in a single axial CT section. These recent efforts are limited due to segmentation of tumors only on a single slice, or in a single organ (e.g. in the lung) for tumor screening, as opposed to advanced stage subjects that will suffer from a higher and more variable tumor burden.

As described herein, techniques are used to analyze one or more image scans of a subject (e.g., such as CT or MRI scans). Each image scan can include a set of images corresponding to a different slice (e.g., a different axial slice). A first neural network can be used to detect, for each image in the image scan, each region that includes a depiction of a particular type of biological object (e.g., a tumor). The first neural network (i.e., an bounding-box detection neural network) can include a convolutional neural network and/or a three-dimensional neural network, such as RetinaNet. The first neural network may be configured to define each region as a bounding box that includes the depicted biological object and potentially a padding of a predefined size (e.g., such that a width of the box is defined to be an estimated maximum width of the biological-object depiction plus two times the padding). The first neural network can be configured to process image scans with an individual focus (e.g., to define regions for each individual image) but using a scan depicting a slice above an individual scan and another scan depicting a slice below the individual scan to provide context.

A second neural network (e.g., a segmentation neural network) can be configured to process smaller portions of the image scan to segment individual objects. More specifically, one or more cropped portions of the image(s) processed by the first neural network can be input to the second neural network. Each cropped portion may correspond to a bounding box defined for a particular image. The cropped portion may have an area that is (for example) equal to an area of the bounding box or an area that is equal to the area of the bounding box plus padding. The second neural network may be configured to receive corresponding portions from other images representing adjacent slices. The second neural network can include a convolutional and/or three-dimensional neural network, such as a UNet. An output of the second neural network can identify, for each box, a set of pixels that are estimated to correspond to a circumference or area of a cross section of the object cross-section depicted in the image.

In some instances, the object segmentations are aligned and/or smoothed across images. Three-dimensional representations of individual objects may then be obtained.

A neural network (e.g., the first neural network, the second neural network or another neural network) can be configured to estimate an environment of the object. For example, the network may output a probability that the biological object is within a subject's lung, liver, bone, mediastinum or other location. The probabilities may be independently assessed (e.g., and the probabilities then need not sum to 1 across the various probabilities). Predicting the context may facilitate segmentation, alignment and/or other processing. For example, a particular type of biological object (e.g., tumor) may generally have different characteristics in different environments. Thus, an environment prediction may inform what types of image features are used to generate object segmentation and/or perform other image processing. In some instances, the network outputs an estimated probability of the image truly depicting an object of a particular type.

In some instances, a third neural network can determine an environment of the biological objects by performing a second segmentation of locations of interest within the images. For example, the third neural network may output segmentations (e.g., in the form of 2-dimensional and/or 3-dimensional masks) of a lung, a liver, a kidney, and/or another location corresponding to a subject. In some instances, a third neural network may be trained to segment a single location of interest, and additional neural networks may be configured to segment additional locations of interest. For example, a third neural network may output segmentations for a lung, a fourth neural network may output segmentations for a liver, and a fifth neural network may output segmentations for a kidney.

Using either two-dimensional segmentations or three-dimensional segmentations, one or more object-specific statistics can be generated to characterize each estimated object depiction. The one or more object-specific statistics can include (for example) an area, longest dimension length or circumference length. One or more scan-specific statistics can be generated for each scan. A scan-specific statistic can include (for example) a number of objects detected per scan, a statistic based on a number of objects detected per scan (e.g., an average, median or maximum), a statistic based on object-specific statistics (e.g., an average, median or maximum) or a statistic based on a volume of objects detected across each scan (e.g., an average, median or maximum). Subject-level statistics may further be generated for a given subject, such as (for example) a total number of objects detected across all scans (e.g., associated with the given subject), a sum of longest dimension length of objects detected across all scans, and/or a cumulative volume of objects detected across all scans.

The scan-specific, object-specific statistics, and/or subject-level statistics can be output. In some instances, statistics can be stored in association with a time point and subject identifier. The statistics can then be tracked and compared over time to estimate a degree to which a medical condition is progressing, an efficacy of a given treatment and/or a prognosis for a given subject.

II. Definitions

As used herein, a "medical image" refers to an image of an interior body of a subject. A medical image can include a CT, MIII, and/or x-ray image. A medical image may depict part of a tissue, an organ, and/or an entire anatomical region of the subject. A medical image can depict part of the subject's torso, chest, abdomen and/or pelvis. A medical image may depict the whole body of a subject. A medical image can include a two-dimensional image.

As used herein, a "whole-body imaging" refers to collecting a set of images that collectively depict a whole body of a subject. The set of images may include images associated with virtual "slices" spanning from a first end (e.g., anterior end) to a second end (e.g., posterior end) of the subject. The set of images may include virtual slices at least a brain region, a chest region, an abdominal region, and a pelvic region of the subject.

As used herein, an "image stack" refers to a set of images that depict a set of adjacent virtual slices. Thus, the set of images may be associated with (for example) different depths. The image stack may include (for example) at least 2 images or at least 3 images. The image stack may include a bottom image, middle image and top image, where a depth associated with the middle image is between the depths of the bottom and top images. The bottom and top images may be used to provide contextual information relevant to processing of the middle image.

As used herein, a "biological object" (e.g., also referred to as an "object") refers to a biological structure and/or one or more regions of interest associated with the biological structure. Exemplary biological structures may include one or more biological cells, organs, and/or tissues of a subject. An object may include (but is not limited to) either these identified biological structures and/or similar structures within or connected to the identified biological structures (e.g., a plurality of tumorous cells and/or tissues identified within a larger body of normal cells, an organ and/or a tissue of a subject).

As used herein, a "mask" refers to an image or other data file that represents a surface area of a detected object or other region of interest. A mask may include pixels of nonzero intensity to indicate one or more regions of interest (e.g., one or more detected objects) and pixels of zero intensity to indicate background.

As used herein, a "binary mask" refers to a mask in which each pixel value is set to one of two values (e.g., 0 or 1). Zero intensity values can indicate that corresponding pixels are part of a background, and non-zero intensity values (e.g., values of 1) can indicate that corresponding pixels are part of a region of interest.

As used herein, a "3D mask" refers to a complete surface area of an object within a 3-dimensional image. Multiple binary masks of an object may be combined in order to form a 3D mask. The 3D mask may additionally provide information about an object's or other region of interest's volume, density, and position in space.

As used herein, "segmentation" refers to determining a location and shape of an object or region of interest within an (2-dimensional or 3-dimensional) image or other data file. Segmentation may involve determining a set of pixels that depict an area or perimeter of the object within the image. Segmentation may involve generating a binary mask for an object. Segmentation may further involve processing multiple binary masks corresponding to the object in order to generate a 3D mask of the object.

As used herein, a "segmentation boundary" refers to an estimated perimeter of an object within an image. A segmentation boundary may be generated during a segmentation process where features of the image are analyzed to determine locations of the edges of the object. The segmentation boundary may further be represented by a binary mask.

As used herein, a "treatment" refers to a prescribing or administering a therapy, medication and/or radiation and/or prescribing or performing a surgical procedure with an aim of treating a medical condition (e.g., to slow progression of the medical condition, to stop progression of the medical condition, to reduce a severity and/or extent of the medical condition, and/or to cure the medical condition).

III. Exemplary Interaction System

FIG. 1A illustrates an exemplary interaction system for using collecting and processing medical images in order to using a multi-stage neural-network platform. In this particular example, the interaction system is specifically configured to locate and segment depictions of tumor biological structures and organs within the medical images.

A. Input Data

One or more imaging systems 101 (e.g., a CT machine, an MRI machine, and/or an x-ray machine) can be used to generate one or more sets of medical images 102 (e.g., CT, MM, and/or x-ray images). Imaging system(s) 101 can be configured to iteratively adjust a focus and/or position as multiple images are collected, such that each image in a set of images is associated with a different depth, position and/or perspective relative to other images in the set. Imaging system 201 can include a light source (e.g., a motorized and/or x-ray source), a light detector (e.g., camera), a lens, an objective, a filter, a magnet, shim coils (e.g., to correct inhomogeneities in the magnetic field), a gradient system (e.g., to localize a magnetic-resonance signal) and/or an RF system (e.g., to excite a sample and detect a resulting nuclear magnetic resonance signal).

Each set of images 102 can correspond to an imaging session, session date and subject. The subject can include a human or animal subject. The subject may have been diagnosed with a particular disease (e.g., cancer) and/or have one or more tumors.

Each set of images 102 can depict an interior of a corresponding subject. In some instances, each image depicts at least a region of interest of the subject (e.g., one or more organs, a chest region, an abdominal region, and/or a pelvic region).

Each image of the set of images 102 may additionally have a same viewing angle, such that each depicts a plane that is parallel to other planes depicted in other images in the set. In some instances, each of the set of images may correspond to a different distance along an axis that is non-parallel to (e.g., perpendicular to) the plane. For example, the set of images 102 may correspond to a set of horizontal virtual slices that correspond to different positions along an anterior-posterior axis of the subject. The set of images 102 may be (e.g., collectively or individually) pre-processed. For example, pre-processing can include normalizing pixel intensities, aligning images to each other or to another reference point/image, cropping images to a uniform size, and/or adjusting a contrast to differentiate between light and dark pixels. In some instances, the set of images 102 may be processed to generate a 3-dimensional (3D) image structure. The 3D image structure may then be used to generate another set of images that correspond to a different angle for virtual slices.

B. Training Data

Some medical images collected by at least one of imaging system(s) 101 can include training images that are to be included in a training data set to train one or more neural networks (e.g., a bounding-box detection network and a segmentation network). Training images may be associated with other subjects as compared to a subject for which the trained network(s) are used.

Each training image can have one or more characteristics of the medical images 102 described herein and can be associated with annotation data that indicates whether and/or where the image depicts a tumor and/or an organ. To identify this annotation data, an image collected by imaging system 101 can be availed to (e.g., transmitted to) an annotator device 103.

The image may be presented at annotator device 103, and an annotator user (e.g., such as a radiologist) may provide input using (for example) a mouse, track pad, stylus and/or keyboard that indicates (for example) whether the image depicts any tumor (or organ of one or more particular types); a number of tumors depicted in the image; a number of tumors that are being annotated (e.g., outlined) by the annotator; a perimeter of each of one or more tumors and/or organ of one or more particular types.

Annotator device 103 may translate the input into (for example) label data 104. Each label data set can be associated with a corresponding image data set. Label data 104 can indicate whether an image contains a tumor and/or one or more particular types of organs. Label data 104 can further indicate where the tumor(s) and/or organs are located within the image by identifying spatial features (e.g., a perimeter and/or an area) of the tumor(s) and/or organs. For example, label data 104 may include a set of coordinates that identify coordinates associated with a perimeter of each of a set of depicted tumors. As another example, label data 104 may include an indication as to which pixels (or voxels) in a training image correspond to a perimeter and/or area of the depicted tumor.

Spatial features may additionally be identified for multiple objects. In some instances, label data 104 may (but need not) identify spatial features of all tumors, organs, and/or other biological objects depicted within the training image. For example, if a training image depicts 10 tumors, label data 104 may identify a perimeter for each of the 10 tumors, or for just 2 of the depicted tumors. In such cases, the incomplete subset of objects may (but need not) be selected based on a predefined selection criteria. For example, an annotator user may have been instructed to only mark depictions of tumors that meet a threshold tumor length and/or a threshold tumor volume and/or within a region of interest (e.g., within one or more specific organs).

Label data 104 may further identify a tumor classification, which may represent a type, a location, and/or size of a tumor as identified based on input from an annotator. For example, a particular label may indicate that a depicted tumor is within a region of an image 102 as corresponding to a specific organ (e.g., a liver). Label data 104 may further include a probability that a particular label actually corresponds to a tumor or an organ of interest. Probability values can be calculated based on a tumor length, a tumor volume, a location with the subject, and/or a number of annotation users that identify the particular label as corresponding to a tumor or organ. Label data 104 can be used to train one or more neural networks to detect, for each image in the image scan, each region that includes a depiction of a tumor or organ. Trained neural networks may be configured to delineate each region identified as including the depicted tumor or organ by processing image scans with an individual focus (e.g., to define specific regions for each individual image) using image stacks corresponding to each of the respective scans.

C. Bounding-Box Detection Network

A neural network processing system 120 can be configured to receive one or more sets of images 102 and corresponding label data 104. Each image of the one or more sets of images may initially be preprocessed by a preprocessing controller 105. For example, one or images depicting different regions of a subject may be stitched in order to generate an aggregated image depicting all of the different regions. In some instances, an aggregated image depicts a "whole body" view of a subject. As another example, one or more images may be scaled and/or cropped to a predefined size. In yet another example, one or more images may be aligned to another image included within the set or to a reference image (e.g., using an alignment marking in the image, a correlation-based technique, or an entropy-based technique). In another example, pixel intensities of one or more images may be adjusted via normalization or standardization methods. In some instances, the sets of images 102 do not undergo any preprocessing techniques.

The preprocessed image(s) may be availed to a bounding-box detection controller 106, which can control and/or perform all of the functions and operations of a bounding-box detection network, as described herein. The bounding-box detection network may be a convolutional neural network, a de-convolutional neural network, or a three-dimensional neural network, that is configured to identify a region (e.g., bounding box) within the set of images 102 that includes a depiction of a tumor. Regions identified by the bounding-box detection neural network may include one or more rectangular or hyperrectangular regions.

Bounding-box detection controller 106 can use the training images and corresponding annotations to train the bounding-box detection network to learn a set of detection parameters 107. Detection parameters 107 can include weights between nodes in a convolutional network. A penalty function may be set to introduce penalties when part of a detected bounding box fails to fully include a depiction of a tumor and/or when padding between a further horizontal and/or vertical point is less than a lower threshold and/or greater than an upper threshold. In some instances, a penalty function is configured to penalize for boundary boxes that are larger or smaller than a predefined zoom range. A penalty function may include a focal loss. Focal loss (as defined in Lin, T. Y., Goyal, P., Girshick, R., He, K., Dollar, P. "Focal loss for dense object detection." *ICCV* 2017, pp. 2980-2988 (2017), which is hereby incorporated by reference in its entirety for all purposes) may be used to deal with class imbalances as well as to ' refocus' the training of the detection task towards hard-to-predict cases resulting from tag perceptual variability in tumors.

Training may be conducted and/or the bounding-box detection network can be defined using one or more fixed hyperparameters. For example, hyperparameters can include a learning rate, number of nodes per layer, number of layers, etc.

The bounding-box detection network can detect one or more bounding boxes 108 corresponding to potential tumor depictions within each of the images 102. Detection of a boundary box may include using an image stack for each image in order to locate a bounding box. For example, if 100 images were collected during a particular imaging session (sequentially numbered in accordance with imaging depth), an image stack can be defined to include a sixth image, seventh image and eighth image when detecting boundary boxes within the seventh image. The image stack may include more than one adjacent images in one or more directions (e.g., so as to include the third through eleventh images when detecting boundary boxes within the seventh image).

Features of the image stack are used to provide contextual information when determining whether and/or where one or more regions include a tumor and/or organ(s). The features can include three-dimensional features that extend across images within an image stack. For example, if a feature (e.g., a learned feature) is present in a similar location(s) throughout an entire image stack (e.g., a combination of a top virtual slice, a bottom virtual slice, and a central virtual slice), the bounding-box detection network may determine that the image region corresponding to (e.g., that includes) the feature represents a bounding box for a tumor. As an alternate example, if a feature of a central slice of an image stack is not present in either a top slice or a bottom slice of the image stack, the bounding-box detection network may determine that the image region corresponding to the feature corresponds to background (i.e. any biological structure other than a tumor) of the image and does not indicate a bounding-box. In some instances, the bounding-box detection network may additionally assign a probability value to each detected bounding box. If the probability value for a bounding box does not exceed a threshold, the bounding box may be discarded as background.

The bounding-box detection network may further process each detected bounding box 108, such that the margins of the bounding box include at least an amount of padding (e.g., 10 px, 15 px, or another suitable amount) from each edge of the region corresponding to the tumor. In some instances, the amount padding is predefined (e.g., so as to generate an initial box that intersects with pixels furthest to the left, top, right and bottom of the detected object depiction and extend the box using a predefined padding or until an image boundary is encountered). In other instances, varying degrees of padding are added so as to maintain uniform bounding-box sizes.

Bounding-box data 108 may include a definition of each bounding box (e.g., as two or more corner coordinates, coordinates of one or more edges, etc.) and/or one or more identifiers of a corresponding image or image set (e.g., an identifier of an image, subject, imaging date, etc.).

It will be appreciated that a location of a boundary box in one image may relate to a location of a boundary box in another image. An image stack may be used to convey this dependence, though other processing may further or alternatively be used. For example, an input to the bounding-box detection neural network may include an identification of each of one or more boundary boxes detected from a previously processed image (corresponding to a same imaging session and same subject). As another example, boundary-box outputs may be post-processed to modify (e.g., translate, resize, delete or add) a boundary-box detection corresponding to one image based on boundary-box detections from one or more other adjacent images.

Figure 1B:
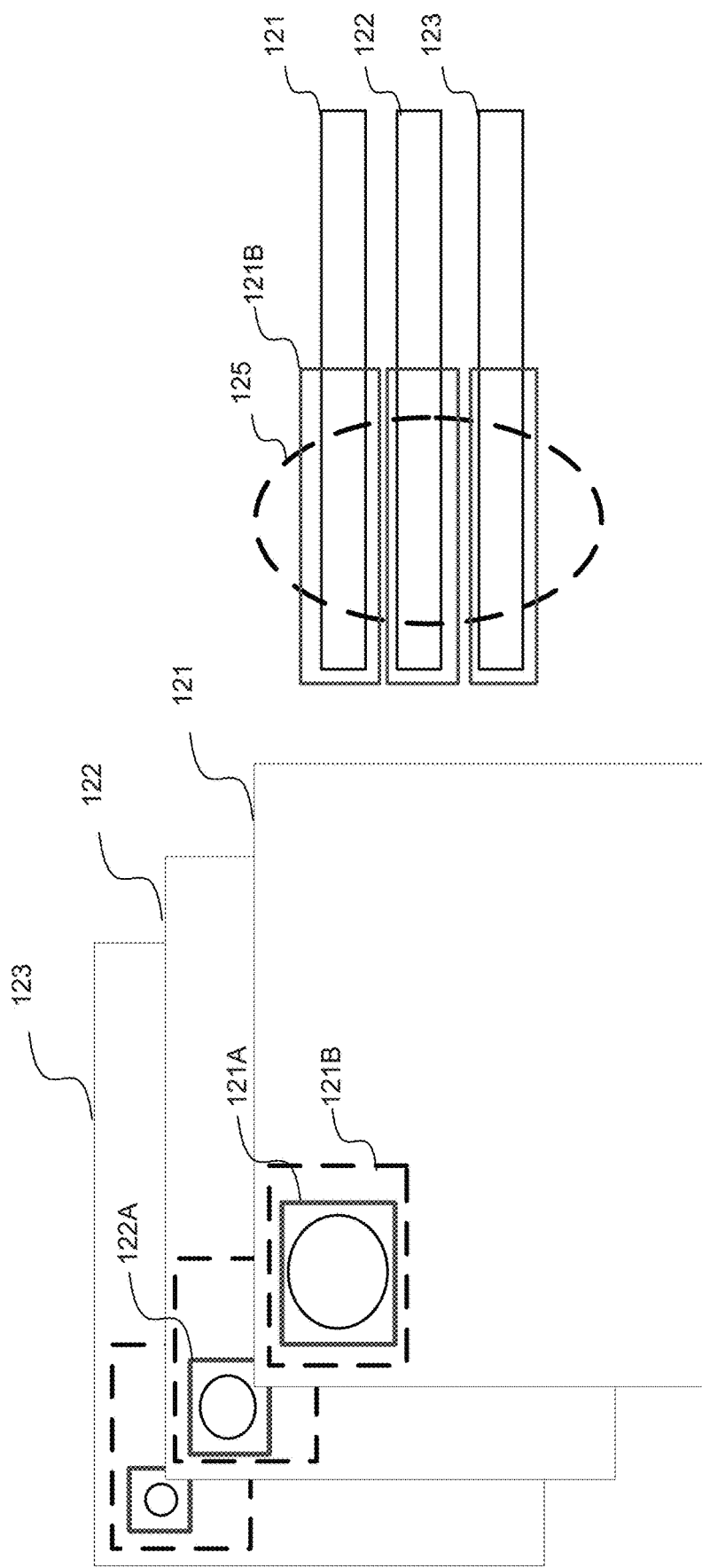
FIG. 1B illustrates an exemplary image stack which includes a set of patches and bounding boxes for a detected biological object.

FIG. 1B shows an exemplary image stack that depicts a set of bounding boxes for a single biological object 125. The image stack may include at least at least an image 121, an image 122, and an image 123 with each image of the image stack depicting a different axial perspective of a region of a subject. In some instances, the image stack may include additional images not shown in the figure. Each image within the image stack may further include a bounding box delineating a possible location of biological object 125 within the particular image, such that each bounding box may be related to the corresponding bounding box(es) included in the other images within the image stack, because each bounding box identifies a presence of the same biological object 125. For example, image 121 contains a bounding box 121A that covers at least a portion of image 121 and image 122 contains a bounding box 122A that covers at least a corresponding portion of image 122, such that bounding box 121A and bounding box 122A are related bounding boxes, and include regions that have been predicted to depict a first possible location and a second possible location of the biological object 125 from a first axial perspective and a second axial perspective, respectively. In other instances, biological object 125 may not be detected within at least a subset (e.g., one or more) of images within the image stack, and the subset of images within the image stack may therefore not include a related bounding box for biological object 125.

There may further be differences within an exact location (e.g., represented by a set of coordinates), a surface area, and/or a shape of related bounding boxes within an image stack. In this example, a surface area of bounding box 121A may be less than than a surface area of bounding box 122A, because a greater portion of the biological object 125 is estimated to be located within image 122. Locations of each of the related bounding boxes may additionally include one or more variations (e.g., in an x-plane, a y-plane, or both) that account for corresponding locations of the same biological object 125 from one or more different axial perspectives of the images within the image stack.

In some instances, responsive to identifying a set of related bounding boxes for an image stack, a detection area is determined for each of the related bounding boxes. For example, an image 121 may include a detection area 121B which surrounds bounding box 121A. Detection areas may be a same size and within a same location for each image within the image stack. In some embodiments, a size and location of a detection area may be determined from a location of a bounding box within a central slice (e.g., in this case, image 122) of the image stack. Detection areas may be configured to include an entirety of each of the identified bounding box along with additional padding. In some instances, detection areas may be determined by another neural network separate from the bounding-box detection network.

D. Tumor Segmentation Network

Referring back to FIG. 1A, bounding-box data 108 may be transmitted to a tumor segmentation controller 109, which can control and/or perform all of the functions or operations of a tumor segmentation network, as described herein. The tumor segmentation network may be trained using a training data set of at least the predicted bounding box data determined during training of the bounding-box detection network. A set of segmentation parameters 110 (e.g. weights) may be learned during training. In the depicted instance, the tumor segmentation network can be (for example) a neural convolutional neural network or a three-dimensional neural network, that is configured to detect and segment depictions of tumors. In some instances, the tumor segmentation network does not include a neural network and may instead use (for example) a clustering technique (e.g., K-means technique), histogram-based technique, edge-detection technique, region-growing technique and/or graph-partitioning technique. The tumor segmentation network may be configured to segment a tumor within each of the detected bounding boxes 108.

For each medical image within the set of images 102, bounding boxes 108 include (for example) one or more portions of the image that correspond to a bounding box(es), or an entirety of the image along with an identification (e.g., vertices' coordinates and/or edge coordinates) of the boundary box associated with the respective image. In some embodiments, interim processing (not shown) can be performed to generate a cropped set of images (e.g., referred to herein as detection areas) corresponding only to the region(s) of the images 102 enclosed by a bounding box 108. In instances in which multiple bounding boxes are defined for a given image, the tumor segmentation network can receive, as input, each corresponding detection area and process the detection areas separately.

Detection areas may provide an focused view of a target tumor as depicted within FIG. 1B. In some instances, detection areas may be of a predefined size. In such instances, a detection area may include another set of regions adjacent to the region corresponding to a bounding box as additional padding in order to maintain a predefined size of the detection area. In other instances, if a bounding box is larger than the predefined size (e.g., 400 pixels or 200 pixels×200 pixels), a region corresponding to a bounding box is partitioned into more than one windows (e.g., of and/or no larger than the predefined size), such that each window corresponds to a separate detection area. In such instances, detection areas corresponding to a single bounding box may include overlapping portions of an image.

If a bounding box extends throughout an image stack (as shown in FIG. 1B), a separate detection area may be defined for each image within the image stack. In some embodiments, processing of the detection areas is performed by the bounding-box detection network prior to transmitting the bounding-box data 108 to the tumor segmentation controller 109.

The tumor segmentation controller 109 implements the tumor segmentation network which is configured to further identify and assess features (e.g., variation in pixel intensities) for each detection area to identify a perimeter, set of edges and/or contours corresponding to the tumor. The features identified by the tumor segmentation network may have similarities to and/or may be different than features identified by the bounding-box detection network. Though both networks may be trained to identify regions of an image that correspond to a tumor, different features may be useful to detect a relatively small structure as compared to relatively large structure. In some instances, the tumor segmentation network may learn to detect a location of an object by (for example) analyzing pixel intensities, a pixel colors, and/or any other suitable image features. As an example, the tumor segmentation network may identify an edge of an object by analyzing an image to detect regions having high contrast, large intensity ranges and/or high intensity variations (e.g., as determined by comparing region-specific metrics to a predetermined threshold value). The tumor segmentation network may include nodes that correspond to different receptive fields (and thus that analyze representations of different collections of pixels). Thus, the network may learn to detect and use at least some different types of features.

In some instances, the tumor segmentation network may utilize the spatial context provided by other images within an image stack to identify the set of edges and/or contours corresponding to the tumor. The image stack can include (for example) three images, with a center image being the one in which tumors are to be detected.

The tumor segmentation network may further generate a 2-dimensional (e.g., binary) tumor mask 110 corresponding to an entire surface area of the tumor within a given detection area using the identified edges and/or contours. A tumor mask 110 may be defined to have values of zero across pixels that are not identified as depicting any part of the tumor. Pixels that are identified as depicting a part of the tumor may be assigned a value of one (e.g., for a binary mask) or another value.

In some instances, a binary tumor mask 110 is generated for each image in an image stack, such that each binary tumor mask 110 corresponds to a different axial perspective of the tumor. In such instances, a post-processing controller 111 can aggregate the set of binary tumor masks 110 to construct a 3D tumor mask 110 representing the tumor's 3-dimensional positioning and shape.

E. Organ-Specific Segmentation Network

In some instances, the neural network processing system 120 can include an organ segmentation controller 111 configured to implement an organ-specific segmentation network. The organ-specific segmentation network can include (for example) a convolutional neural network and/or a three-dimensional neural network. Exemplary convolutional neural networks may include a VGG 16, a U-Net, and/or a ResNet18 network. The organ-specific segmentation network may be configured to analyze medical images corresponding to a subject and to segment one or more organs depicted within the images. In such instances, each of one or more organ-specific segmentation networks can be configured (e.g., via parameters learned during training) to segment a particular type of organ. Exemplary organs of interest may be (for example) a liver, or a lung, or a kidney, or a pancreas, etc.

In some instances, the organ-specific segmentation network may be configured to perform a series of convolutions, such as depthwise and pointwise-convolutions, as part of a segmentation process. In such instances, one or more inflations along a particular dimension may further be performed. The particular dimension may be a third dimension, a fourth dimension, etc. In some instances, the tumor segmentation network may also apply one or more filters, such as a replicate filter.

In the depicted instance, organ segmentation controller 111 can control an organ-specific segmentation network configured to detect a particular type of organ. The organ-specific segmentation network can be trained using a training data set that includes training images and annotations that indicate which portions, within each of at least some of the training images, depict the particular type of organ. The training data set may be separate from the training data set used by the bounding-box detection network and the tumor segmentation network. The training data set can include multiple medical images and corresponding annotations and/or segmentation boundaries (e.g., generated by an annotator device 103) for the particular organ of interest. A set of organ segmentation parameters 112 (e.g. weights) may be learned during training. In some instances, pre-processing controller 105 may transmit the same set of medical images 102 to both bounding-box detection controller 106 and organ segmentation controller 111.

The trained organ-specific segmentation network can be used to process each of a set of images and/or preprocessed images to detect organs. Images used for detecting the particular type of organ may be the same as (or different than) the set of images 102 provided to bounding-box detection controller 106, such that the images are provided to organ segmentation controller 111 concurrently. The set of images may be divided into multiple (e.g., overlapping) subsets that include 1, 2 or 3 images. For example, subsets may be defined to have three images per subset and a shift of one image per subset. In some instances, the images may undergo preprocessing in order to align the images into a 3D image depicting a "whole body" view of a subject.

Within each image, the organ-specific segmentation network can indicate whether a given image depicts a particular type of organ and further identifies a perimeter of a depiction of an organ. An output of the organ-specific segmentation network can include an organ mask 113 that (for example) has values of zero for pixels not depicting a particular type of organ and non-zero values for pixels depicting a particular type of organ. In some instances, multiple 2-dimensional organ masks corresponding to different virtual slices (e.g., perspectives) of the organ of interest may be generated. These 2-dimensional organ masks may be aggregated to generate, for each organ, a 3D organ mask.

Post-processing controller 114 can individually and/or collectively process tumor masks 110 and organ masks 113 to generate statistics and/or descriptors. For example, for each tumor, post-processing controller 114 can identify a volume of the tumor and can further identify whether the tumor is within any organ (and, if so, which type of organ). Post-processing controller 114 can further process (2- or 3-dimensional tumor masks) to calculate subject-level tumor statistics, such as a total tumor volume and/or density for a subject and/or a sum of longest dimensions. In some instances, a sum of longest dimensions may be a sum of longest diameters, such that a longest diameter is calculated for each tumor and summed to form the total sum of longest diameters. In some instances, post-processing controller 114 can identify a percentage of a mass of the tumor in comparison to a mass of the corresponding organ of interest as another exemplary statistic.

Neural network processing system 120 can output the descriptors and/or statistics to a user device. Further, a representation of one or more tumor masks and/or one or more organ masks may be transmitted. For example, an image may be generated that includes a depiction of an original image with overlays that identify a perimeter of each detected tumor and/or organ for a subject. In some instances, post-processing controller 114 may further process (e.g., or transmit to another model and/or controller for processing) the subject-level tumor statistics to generate a score(s) for a probability of survival using one or more treatment methods.

While the interaction system depicted in FIG. 1A relates to detecting tumors and determining whether various tumors are within different organs, alternative embodiments may relate to detecting other types of biological objects. For example, a first network may be trained to detect brain lesions and other networks can be trained to detect various brain regions, such that it can be determined in which brain region a lesion is located. As such, alternative embodiments may replace at least the tumor segmentation network with a different segmentation neural network trained to segment other biological structures within the medical images.

IV. Prediction Network System

Figure 2:
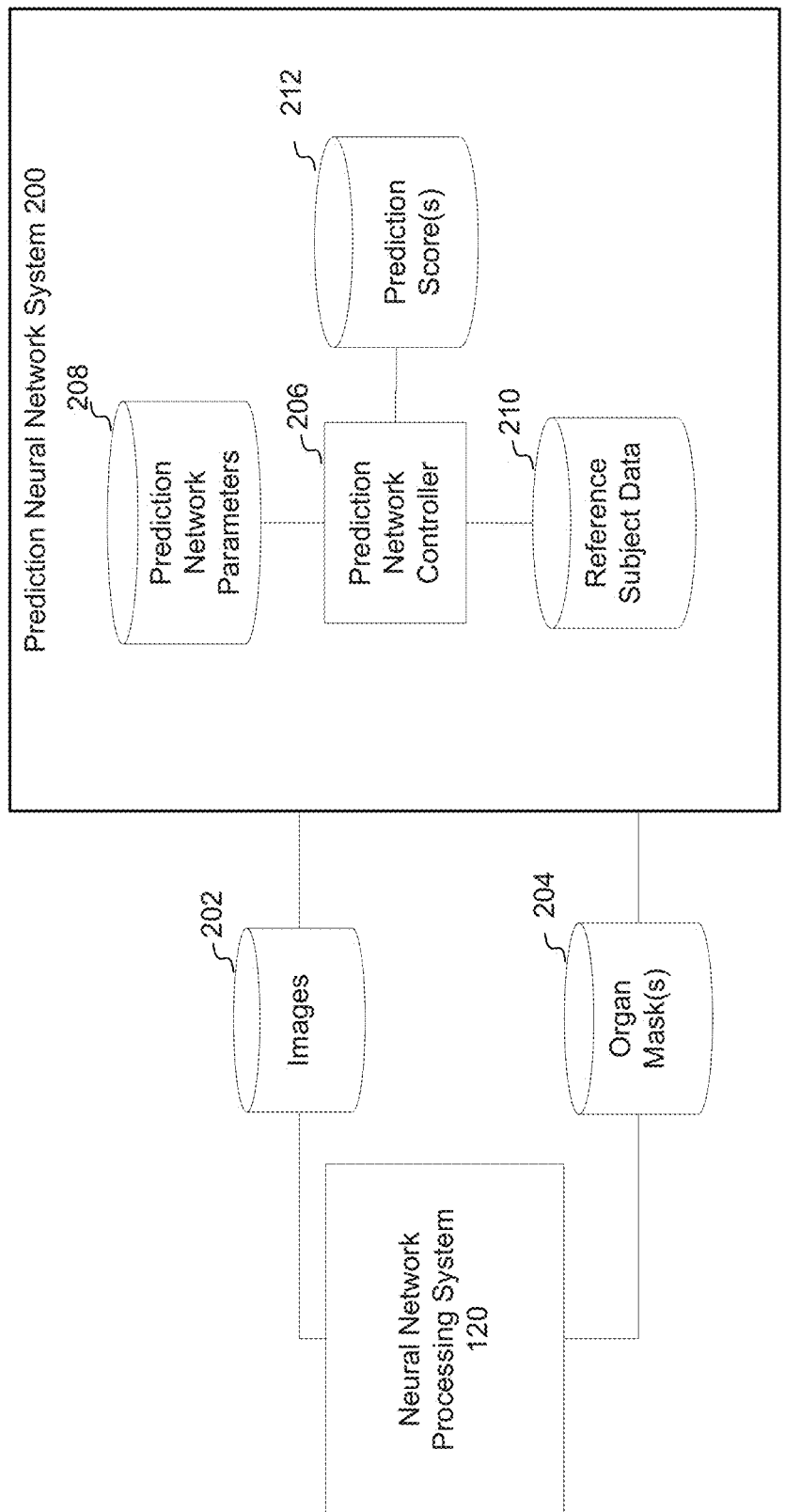
FIG. 2 illustrates an exemplary system for generating one or more pairwise comparisons between two or more subjects.

FIG. 2 illustrates an exemplary prediction neural network system 200 that can use one or more output elements (e.g., organ masks) from the neural network processing system 120 in order to predict a score for a probability of survival of the subject based on an efficacy of a treatment method. Efficacy may be determined by one or more characteristics (e.g., such as a progression of disease, measured in terms of tumor volume or density) of the subject prior to administering the treatment method.

In instances when it is desired to predict these scores, a neural network processing system 120 may avail one or more medical images 202 and organ masks 204 to the prediction neural network system 200. Images 202 may be a subset of the same images used by a bounding-box detection network and a tumor segmentation network as discussed in Section III. In some instances, images 202 may additionally include corresponding metrics, such as a count, a volume, and/or a location of tumors. Organ masks 204 may additionally include at least one or more organ masks generated by an organ-specific segmentation neural network. In some instances, the neural network processing system 120 may additionally avail tumor masks (not depicted in figure) that had been generated by the tumor segmentation network to the prediction neural network system 200.

In the depicted instance, a prediction network controller 206 may be configured to control and/or perform any of the operations, as described herein, of a prediction neural network, which may be a neural network that is different from the bounding-box detection network and the tumor segmentation network described in the neural network processing system 120. Prediction network controller 206 can train the prediction neural network to predict survival or mortality rates associated with one or more treatment methods for a subject, using images corresponding to one or more sets of comparable pairs of subjects.

A pair of subjects may be considered comparable if (for example) a first subject and a second subject have both received a same treatment method and the first subject has a different period of survival after receiving the treatment compared to the second subject. Conversely, a pair of subjects are not considered comparable if the first subject has an first period of survival that is inconclusive, such that the first period of survival was only tracked for a particular time period (e.g., for a length of a clinical trial) but no additional data related to the first period of survival was collected after the particular time period, and the second subject has a second period of survival that is at least after the particular time period for which the first period of survival was tracked. Therefore, not every possible pairing of subjects may be considered comparable.

During training, a set of prediction parameters 208 (e.g., weights) may be determined for the prediction neural network. Training data elements may include at least one or more input images or metrics (e.g., a cumulative volume for all detected biological objects) associated with each subject of the comparable pairs of subjects and a metric measuring a period of survival for each subject after a treatment has been administered. A score and/or rank based on the period of survival for each subject may also be included within the training data elements. Scores and/or ranks may correspond to a likelihood of survival for a subject using the administered treatment. Training may utilize a loss function that maximizes a difference in the score during training between the subjects of the pair, such that a first subject is determined as having a best chance of survival using the treatment compared to a second subject.

Reference subject data 210 may be a database that includes at least an administered treatment method, a period of survival, and one or more subject-level metrics (e.g., a number of tumors, a location of tumors, a SLD or volume of tumors) for each subject of a plurality of reference subjects, such that each subject of the plurality of reference subjects may further include a subject-level statistic such as a rank based on the period of survival for a single subject in comparison to the plurality of reference subjects. The rank may be a value k ranging from 1 to a total number of subjects within the plurality of reference subjects that predicts a relative mortality risk (e.g., represented as a likelihood that a subject survives after treatment, or an expected period of survival for the subject) for each of the plurality of reference subjects. The period of survival for each subject can be measured from either a diagnosis of a disease or a start of a treatment period for the subject. In some instances, at least some of the plurality of reference subjects may be deceased. Reference subject data 210 may specifically group reference subjects by the administered treatment method.

When predicting a survival rate for a subject of interest using a particular treatment method, the prediction neural network may select one or more reference subjects that meet the criteria for comparability with the subject of interest from the reference subject data 210 to form at least one or more pair of subjects, such that each pair comprises the subject of interest and a different reference subject.

The prediction network may then determine a prediction score 212 for the given subject by comparing the subject of interest to each of the selected reference subject(s). Prediction score 212 may be any suitable metric (e.g., a percentage or a time period) that indicates a probability and/or length of survival for the subject of interest. Comparisons to reference subjects may involve comparing one or more characteristics associated with each reference subject prior to receiving the treatment method to the same characteristics associated with the subject of interest. In some instances, a ranking may be generated for the one or more pairs of subjects, such that a rank value of a subject may indicate the subject's likelihood of survival. For example, a subject with a lowest rank value may be predicted as having a worst likelihood of survival using the treatment method. Rank values may be determined from a total tumor count, volume, or density and/or location(s) of tumors for each subject of the one or more pairs of subjects.

Prediction score 212 may be calculated for the subject of interest based on at least where the subject of interest falls within the ranking in comparison to the reference subjects. It can then be predicted whether and/or to what extent the treatment method may be effective for the subject of interest.

V. Exemplary High-Level Process

Figure 3:
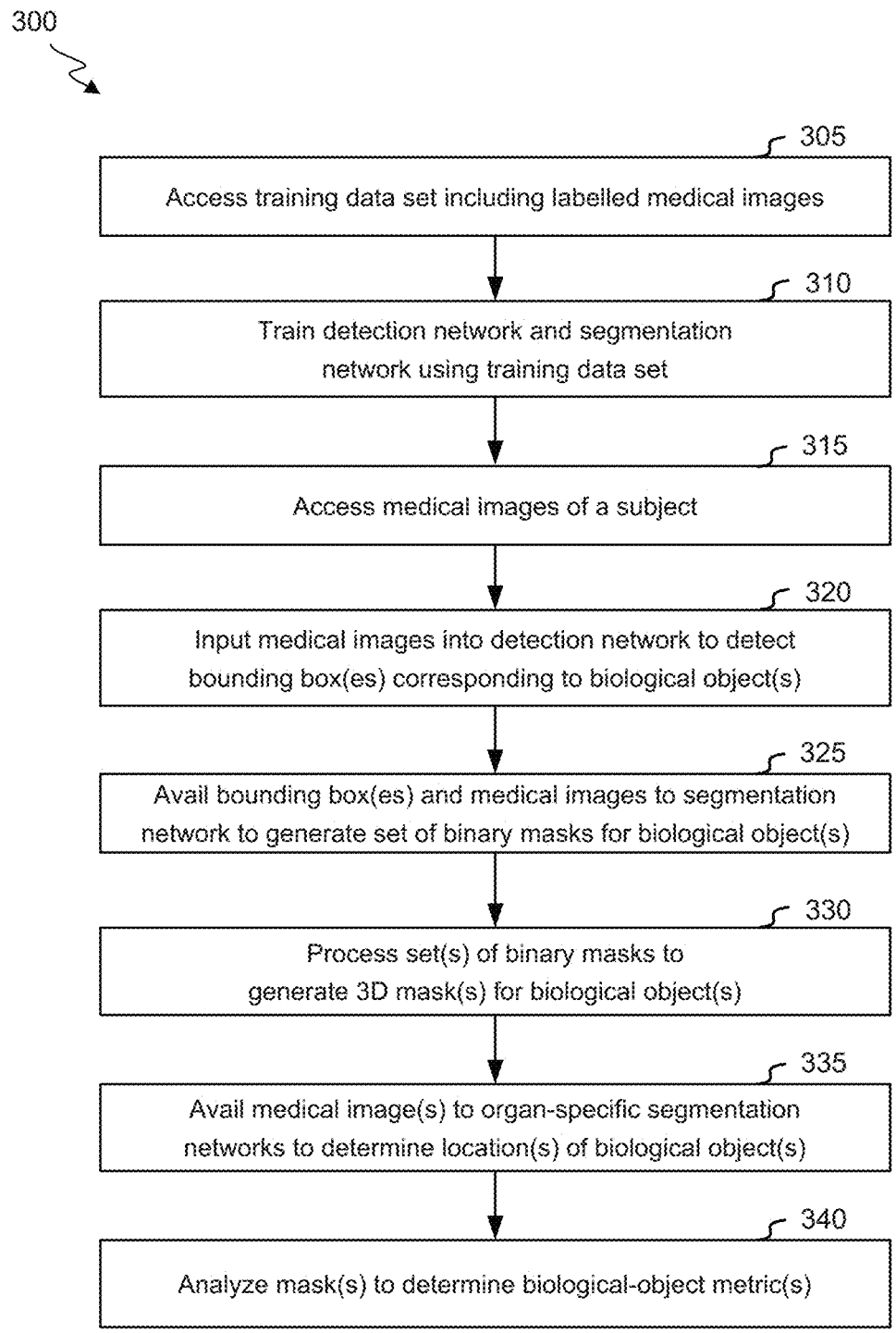
FIG. 3 illustrates an exemplary method for the processing of medical images using the multi-stage neural-network platform.

FIG. 3 illustrates a flowchart of an exemplary process 300 for using a multi-stage neural-network platform to process medical images. Process 300 may be performed using one or more computing systems.

Process 300 begins at block 305 where a training data set is accessed. The training data set includes multiple training elements. Training elements include a set of medical images (e.g., a CT image) corresponding to a subject and annotation data identifying the presence of biological objects within the set of medical images. Annotation data includes a label indicating a presence of a biological object and (if the biological object is present) a general location (e.g., a liver, a kidney, a pancreas, etc.) of the biological object. Annotation data may be incomplete, such that the presence of one or more biological objects is not included. In some instances, a medical image may correspond to two or more different sets of annotation data based on annotations from at least two or more radiologists. In such instances, different sets of annotation data corresponding to a same image include discrepancies such as an identification, or lack thereof, of one or more additional biological objects and/or a difference in an annotation size and/or an object perimeter of one or more biological objects. The training data set may have been generated using one or more imaging systems and one or more annotation devices as disclosed in Section III.

At block 310, a multi-stage neural network platform is trained using the training data set. The multi-stage neural network platform can include a boundary-box detection network and a biological structure segmentation network. In some instances, the neural network platform additionally includes one or more organ-specific segmentation networks.

The bounding-box detection network can be trained to detect bounding boxes for areas corresponding to biological objects. In particular, training the bounding-box detection network involves defining a bounding box for each region corresponding to a biological object within an image. Each of the biological objects can be further labelled in order to indicate that the bounded region corresponds to a given object (e.g., when multiple objects are identified across the set of images. In some instances, a label may also include a location of the biological object within the subject.

The biological structure segmentation network (which is similar to a tumor segmentation network described in FIG. 1A) is trained to identify boundaries and a total area of depicted biological objects. Training of the segmentation network may include accessing an additional training data set. The additional training data set may include all of the training data elements of an initially accessed training data set along with labelled segmentation data generated by a radiologist. Labelled segmentation data may include either a binary mask or a 3-dimensional mask of a biological object. In some instances, the segmentation network is trained to further correct false positive (e.g., mislabeling a background region as an object) generated by the detection network.

Training may further be performed using a pixel-wise cross entropy loss, a Dice coefficient loss, or a compound loss. A loss function can be based on (but is not limited to) a mean square error, a median square error, a mean absolute error, and/or an entropy-based error.

A validation data set may also be accessed to assess a performance of the multiple-stage neural network platform in concurrence with its training. The validation data set may be another set of medical images and corresponding annotation data that is separate from the training data set. If a target accuracy is reached for both the identification and segmentation of biological objects within the medical images for the validation data set, the training session may be terminated.

At block 315, a set of medical images corresponding to a subject and/or a singular imaging session is accessed. The set of medical images may depict a chest region, an abdominal region, and/or a "whole body" region of the subject. In some instances, a first medical image corresponding to a chest region, a second medical image corresponding to an abdominal region, and a third medical image corresponding to a pelvic region may be stitched to generate a fourth medical image corresponding to a "whole body" region of the subject.

Medical images may be generated using one or more imaging systems as disclosed in Section III.A. In some instances, the one or more imaging systems may be configured to generate images corresponding to different perspectives of a region of the subject. In such instances, multiple medical images may depict distinct virtual slices of a particular region.

At block 320, the set of medical images is availed to a bounding-box detection network. Each image is analyzed to identify one or more bounding boxes. Each bounding box can identify an image region corresponding to a target biological object. Analysis of an image may comprise the use of a first virtual slice corresponding to a region and/or a view above the image and a second virtual slice corresponding to a region and/or a view below the image, such that the first virtual slice and the second virtual slice provide additional spatial context for determining a region corresponding to the target biological object.

In some instances, a bounding box may include a set of margins (e.g., for example, a padding of 10 px) surrounding the identified region corresponding to the target biological object. If more than one region corresponding to a biological object is identified within an image, the bounding-box detection network may identify more than one bounding boxes for the image.

At block 325, one or more bounding boxes corresponding to the medical images are availed to a segmentation network. The segmentation network can crop the medical images to generate a set of detection areas depicting a zoomed-in view of each region corresponding to a bounding box. Detection areas may be assigned a uniform size, such that a detection area may include additional padding along with a region corresponding to a bounding box if the region is smaller than the uniform size. In the event that the region is larger than the uniform size, the region corresponding to a bounding box may be divided into more than one detection areas. In the case of multiple detection areas corresponding to a bounding box, a region corresponding to a bounding box may be partitioned into a set of sliding-windows, such that some of the windows include an overlapping subset(s) of the region.

For each detection area associated with a bounding box, the biological structure segmentation network can assess image features of the detection area in order to locate a biological object and generate a first binary mask corresponding to the biological object. If multiple bounding boxes are identified for a given image, the biological-structure segmentation network can identify an area within each of the bounding boxes that depicts a corresponding biological object. A binary mask may be generated for each biological object. In some instances, more than one binary mask may be generated for a biological object using images depicting different perspectives of the biological object.

At block 330, one or more binary masks corresponding to the same object can be processed (e.g., via post-processing) to generate a 3D mask. Each of the one or more binary masks and each 3D mask can correspond to a single biological object. Thus, for example, multiple 3D masks may be generated for a given subject's imaging session, with each 3D mask corresponding to one of multiple biological objects.

Processing a set of binary masks can include aggregating the binary masks to form a 3D structure of the object as described in Section III.D. As some of the binary masks may further include overlapping regions, the segmentation network may adjust a region of one or more binary masks to account for the overlapping regions and/or elect to not include one or more binary masks that may depict a redundant perspective.

At block 335, the medical image (e.g., as accessed from block 315) corresponding to the one or more masks is availed to one or more organ-specific segmentation networks to determine a location of a biological object. Each organ-specific segmentation network may correspond to a particular organ of interest (e.g., a liver, a kidney, etc.) and may be trained to identify the particular organ of interest within an image. An organ-specific segmentation network may receive and process the set of images to identify a location of a corresponding organ of interest. If the corresponding organ of interest is detected, the network may additionally generate a mask of the corresponding organ. The generated organ mask may be a binary mask and/or a 3-dimensional mask.

At block 340, one or more masks (e.g., one or more 3D biological-object masks, one or more 2-dimensional biological-object masks and/or one or more organ masks) are analyzed to determine one or more metrics. The metric(s) can include a characteristic of the biological object(s). For example, the metric(s) can include an object count, a location and/or type of an object, a count of objects for a particular location and/or type, a size of one or more objects, an average size of the objects, a cumulative size of the objects, and/or a number of objects within each of one or more types of tumors.

In some instances, the metric(s) include one or more spatial attributes of the object, such as a volume of an object, a length of an object for a longest dimension, and/or a cross-sectional area of an object. One or more spatial attributes may further be used to generate subject-level statistics for all objects detected within a given subject. Subject-level statistics may include (for example) a cumulative object volume for a given subject, a sum of object lengths for a longest dimension for a given subject (e.g., such as a sum of longest diameters), and/or a cumulative cross-sectional area of detected objects for a given subject.

In some instances, a metric is compared to another metric associated with medical images of a same subject collected during a previous imaging date to generate a relative metric (e.g., percentage or absolute change). The metric(s) may be output (e.g., transmitted to another device and/or presented to a user). The output may then be analyzed by (for example) a medical professional and/or radiologist. In some instances, the metric(s) are output along with a depiction of one or more masks.

The metric(s) can be used to predict (e.g., at a computing system using one or more stored rules and/or via a user) a diagnosis and/or a treatment efficacy for the subject. For example, subject-level statistics, such as a cumulative biological-object volume may be used to determine a disease stage (e.g., by determining a range that corresponds to the cumulative volume). As another example, a relative change in biological-object volume and/or count can be compared to one or more thresholds to estimate whether a current and/or previous treatment was effective.

In some instances, the metrics may be used to predict a score for one or more treatment methods based on a probability of survival for a subject calculated by a prediction neural network. The score may be predicted using one or more spatial attributes, such as a cumulative object volume and/or a sum of a length of longest dimensions for the object(s). In some instances, one or more scores for a probability of survival may be generated to rank a set of subjects and/or treatments. In such instances, a score for a subject and/or treatment may be compared to one or more scores of another subject(s) and/or another treatment(s) in order to determine the rankings. A subject-specific ranking may identify at least one or more subjects with a highest probability of survival for a given treatment relative to other prior subjects that have been administered the given treatment. A treatment-specific ranking may identify a treatment(s) with a highest likelihood of success (e.g., survival) for a given subject relative to other treatments. In some instances, the subject-specific ranking and/or the treatment-specific ranking are also returned as output.

VI. Exemplary Implementations

VI.A. Implementation 1

VI.A.1. Pipeline for Automated Identification and Segmentation of Tumors

Tumor segmentation from whole body CT scans was carried out using an automated method of detection and segmentation consisting of a bounding-box detection network (discussed in Step 1 below) and tumor segmentation network (discussed in Steps 2-3).

VI.A.1.a. Step 1: Bounding-Box Detection

Figure 4:
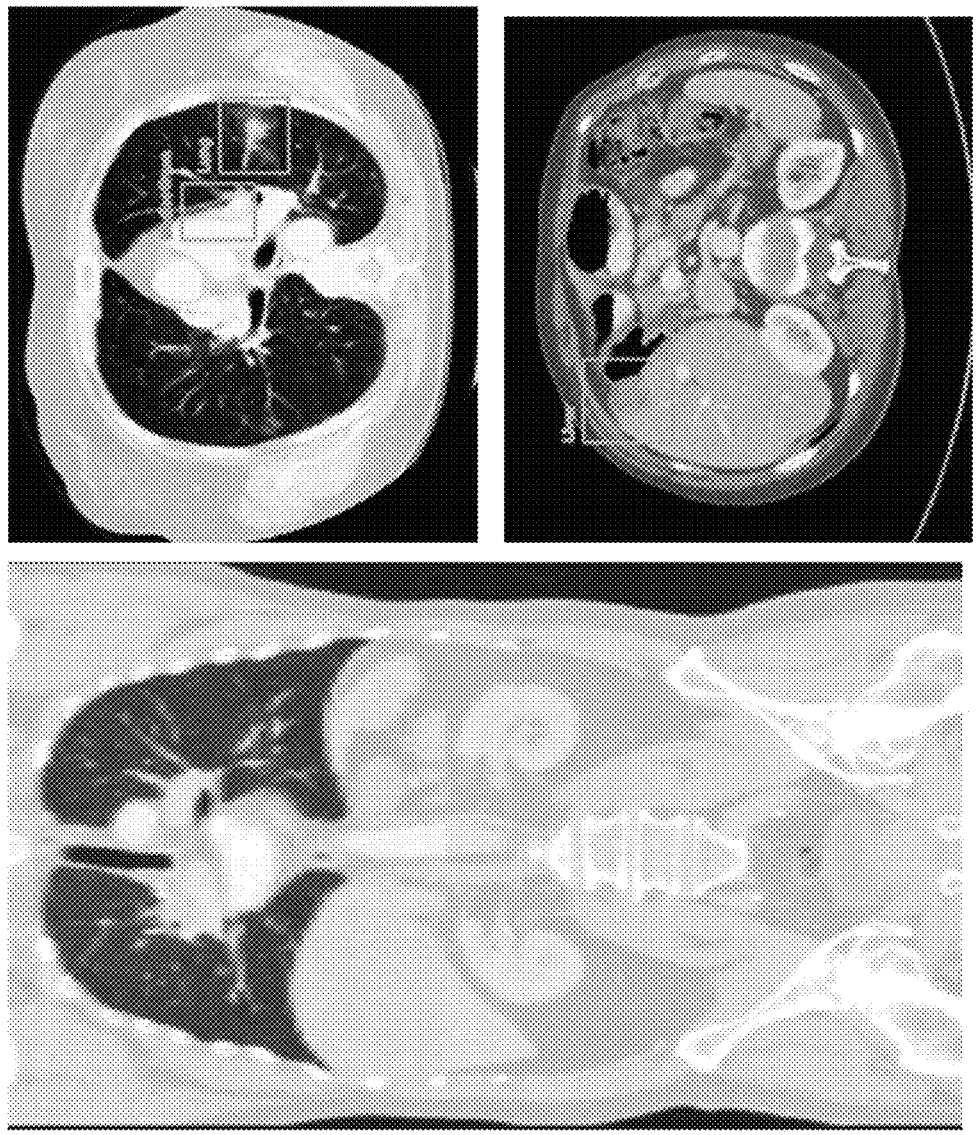
FIG. 4 shows an exemplary set of images for tumor detection. The leftmost panel depicts a whole body scan of axial slices after preprocessing, while the right panels depict the detected bounding boxes, generated and labelled automatically by a bounding-box detection network, for a lung, liver, and mediastinum region within an axial slice.

A bounding-box detection network having a RetinaNet architecture (referred to herein as a "detection network")

was used to predict whether regions of a medical image depict a tumor, generate bounding boxes identifying general spatial locations of tumors within the regions of the image, and provide a probability of a site label for each general spatial location depicting a tumor. In training the detection network, a modification was made from published Retina-Net architectures in that all convolutions were changed to separable convolutions. For each medical image, an image stack comprising a set of three consecutive axial CT slices (with no fixed resolution) was used as input for the detection network. The detection network was trained to detect regions including tumors within each of the slices included within the image stacks, generate bounding boxes for each of the detected regions, and attribute them to one of the following available site labels: Lungs, Mediastinum, Bones, Liver, and other. FIG. 4 illustrates an example set of images depicting (i) a pre-processed whole body scan of a subject; (ii) a bounding box identifying a tumor predicted as corresponding to a Mediastinum site and a bounding box identifying a tumor predicted as corresponding to a Lungs site within an axial slice of a subject; and (iii) a bounding box identifying a tumor predicted as corresponding to a Liver site within another axial slice of a subject.

The detection network outputted (i) proposal coordinates of bounding boxes which represent the general spatial locations of tumors on the middle axial slice; and (ii) the probability of each site label (Lungs, Mediastinum, Bones, Liver, other) category. The outputs were concatenated to have bounding boxes in each slice of the CT scan as shown in FIG. 4. Each of the three consecutive axial CT slices were of size 512×512. Training was performed on 48,000 radiologist-annotated images for axial CT slices with bounding boxes around radiologist identified RECIST target and non-target lesions, with corresponding site locations from 1,202 subjects from the IMPower150 clinical trial. Hyperparameters included a batch size 0.16, learning rate 0.01, and use of the optimizer ADAM. The detection network was validated on the IMpower131 clinical trial (969 subjects). Lesion-level sensitivity on RECIST reads was 0.94. Voxel-level sensitivity was 0.89.

VI.A.1.b. Step 2: Tumor Segmentation

Figure 5:
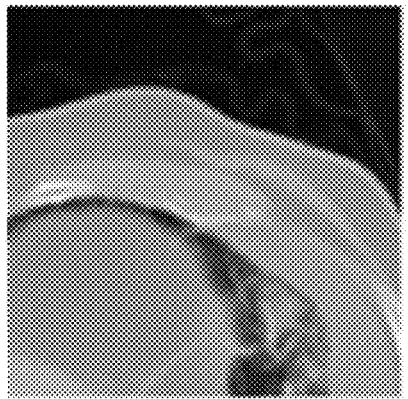
FIG. 5 shows examples of tumor segmentation using axial CT scans. Each of the top panels depict a determined region of a tumor. The correspond bottom panels depict exemplary segmentation boundaries for the tumor.
Figure 5:
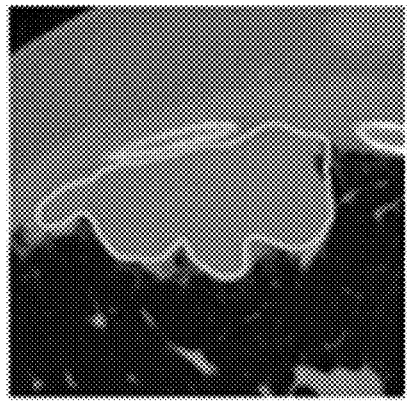
Figure 5:
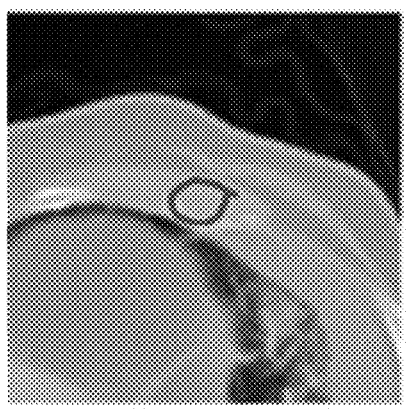
Figure 5:
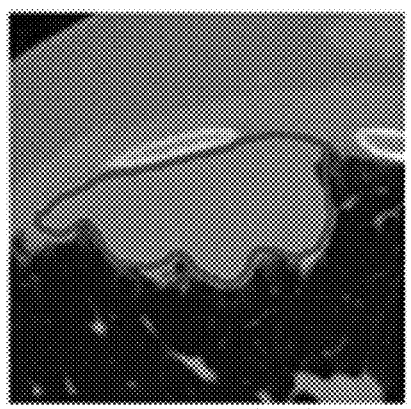
Figure 5:
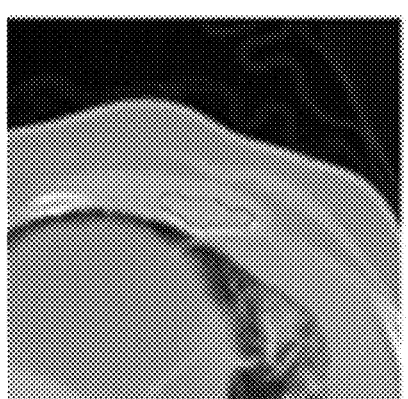
Figure 5:
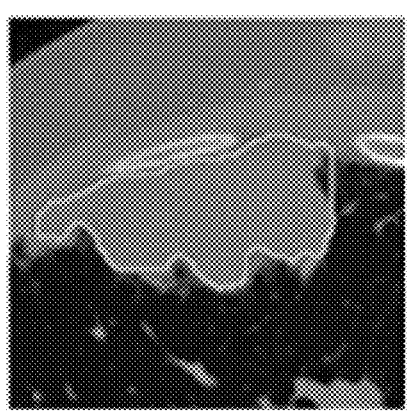

A tumor segmentation network (e.g., which, for this example, was implemented as a probabilistic U-Net) was used to identify an area within each bounding box identified by the detection network (e.g., and/or portions corresponding to regions within which a mask value was positive and/or equal to 1) that depicts a tumor. As shown in FIG. 5, each of the 6 images correspond to a bounding box identified by the detection network, and each of the outlined areas identify a tumor segmentation as determined using the tumor segmentation network. In training the tumor segmentation network, a modification was made from published probabilistic U-Net architectures in that all convolutions were replaced by separable convolutions. The tumor segmentation network was configured to average 16 predictions for the area within each bounding box to mimic inter-reader variability and decrease the variance on the predictions. Therefore, each prediction corresponded to a different method or criteria that different radiologists use when annotating (or choosing not to annotate) a same lesion and the 16 average predictions were then used to generate a "consensus" by averaging predictions for each voxel within an image and determining each voxel as a portion of a tumor if the average predictions were larger than 0.5, or some other threshold value. Three axial slices of 0.7×0.7 mm size (i.e., 256×256 pixels) were used as input for the tumor segmentation network, such that each of the axial slices correlate to a detected bounding box that has undergone one or more interim pre-processing techniques (e.g., cropping).

The tumor segmentation network outputted a segmentation of the middle axial slice which identified the area within each bounding box that depicts a tumor. The tumor segmentation network was trained on 67,340 images with tumor masks from 1,091 subjects in IMpower150 from volumetric RECIST reads from one radiologist and 2D RECIST. Example hyperparameters included a batch size of 4, a learning rate of 0.0001, and use of the optimizer ADAM. The example network was validated on IMpower131 (969 subjects; 51,000 256×256 images with 0.7×0.7 mm images). A dice score (using the average over 16 predictions from the network) of 0.82 was calculated assuming no false positives in the validation dataset (51,000 images from IMpower131).

VI.A.1.c. Step 3: Organ-Specific Segmentation

The segmentations outputted from the tumor segmentation network in Step 2 were used to confirm/correct the general spatial locations of tumors proposed by the bounding-box detection network in Step 1. A subject's whole body CT scan was taken as input for processing by separate organ segmentation networks. In this Implementation, the organ segmentation networks consisted of multiple convolutional neural networks. Each of the separate organ segmentation networks was trained to perform organ-specific segmentations and return organ masks identifying the locations of the organs in the whole body CT scan. Organ-specific segmentation was accomplished by training a different organ segmentation network for each of the organs of interest, for example, right lung, left lung, liver, spleen, kidneys, bones and pancreas. Each of the organ-specific segmentation networks had a 3D U-Net architecture that included batch normalization and leaky ReLU activation at each layer. The organ-specific segmentation networks for the kidneys, spleen and pancreas used publicly available datasets for training, specifically to complete Kits19 (such as the dataset in Heller, N. et al. "The KiTS19 Challenge Data: 300 Kidney Tumor Cases with Clinical Context, CT Semantic Segmentations, and Surgical Outcomes." (2019), which is hereby incorporated by reference in its entirety for all purposes) for kidneys and medical decathlon for spleen and pancreas (as described in Simpson, A. L. et al. "A large annotated medical image dataset for the development and evaluation of segmentation algorithms." (2019), which is also hereby incorporated by reference in its entirety for all purposes). Ground truth for the bone segmentation network was based on morphological operations.

For each of the organ-specific segmentation networks, the input was a 256×256×256 CT volume (of a concatenation of the axial slices from Steps 1-2) resampled to a voxel size of 2×2×2 mm. The output of each of the organ-specific segmentation networks was an organ mask of the same size for each organ. Ground truth for each network was a 256×256×256 corresponding organ mask with same voxel size. Hyperparameters included a batch size of 4, a learning rate of 0.0001, and use of the optimizer ADAM. Data augmentation with combinations of rotations, translations and zooms was used to augment the datasets for more robust segmentations and to avoid overfitting. Initial versions of the organ-specific segmentation networks trained as described herein produced the following results: Lungs: 0.951; Liver: 0.964; Kidneys:

0.938; Spleen: 0.932; Pancreas: 0.815; Bones: 0.917 (ground truth generated using morphological operations).

VI.A.2. Time-Separated Pairwise Comparisons

VI.A.2.a. Overview

CT scans, organ-specific segmentation, and the techniques described herein were further used in conjunction with the automated detection and segmentation of tumors to generate a number of other predictions and estimates to assist clinicians in deciding which treatments to prescribe. Upon identification of one or more tumors and/or a "whole body" tumor burden using the automated pipeline, survival chances of a subject were predicted, given each of a number of potential treatments for a given oncology indication, by models according to one of a number of metrics, in terms of overall survival, progression free survival, or other similar metrics. The models outputted a ranking of treatments for a given subject to identify the treatment that provided the longest survival time. Alternatively, the models outputted a ranking of subjects to identify the subjects likely to experience the longest survival times on a given therapy.

VI.A.2.b. Model Architecture and Training

Given 2 subjects A and B, it was assumed that the outcome (overall survival) would be observed for at least one subject. Without loss of generality, it was assumed that the outcome for subject A that (denoted $T_A$) was observed and that subject B (denoted as $T_B$) is censored or dies at $T_B > T_A$.

Input to the network was a CT scan and organ masks (e.g., Liver, Lungs, Kidneys, Bones, Pancreas and Spleen) obtained using one or more organ-specific segmentation networks for both subjects A and B. The organ-specific segmentations network's architecture was an inflated VGG16, ResNet18, or similar network, with separable convolutions outputting a score vector having N elements (e.g., 1000) for each subject. Inflation was generally performed in accordance with the technique described in Carreira, J and Zisserman, A. "Que Vadis, Action Recognition? A New Model and the Kinetics Dataset" In: CVPR (2017), which is hereby incorporated by reference in its entirety for all purposes. However, in this Implementation, separable convolutions were performed in 2 steps (first a depthwise- followed by a pointwise convolution); however instead of only inflating along the 3rd dimension for a traditional convolution, inflation was broken into 2 steps. For the depthwise convolution, inflation was performed along the third dimension, then replicate filters were applied once and an average was calculated along the fourth dimension (number of input filters). For the pointwise convolution, averages were determined across the first 2 dimensions, inflation was performed along the 3rd dimension and replication was performed the 4th dimension. The above modifications facilitated processing large (by pixel/voxel count) 3D whole body CTs with the network, while achieving functional model performance.

During training, the scores obtained for subjects A and B (SA and SB) were compared. The training procedure aimed at minimizing the loss L=exp(SB)/exp(SB)+exp(SA) over the data sample. Training data included 42,195 comparable pairs of subjects from 818 subjects from the IMpower150 clinical trial, separated by treatment arms. Select hyperparameters included a learning rate (lr)=0.0001, Batch Size=4, and use of the optimizer ADAM. Results for the example model on pairwise comparisons show that 74% of the pairwise comparisons were accurate in a test (validation) set of 143 subjects from the 3 treatment arms of G029436 (IMPower 150). For these results, comparisons were made only on subjects within a treatment arm.

VI.A.3. Results

Performance for the automated method on the training and test data sets was determined using RECIST and manual annotations of a "whole body" tumor burden. RECIST reads were performed on both data sets as a baseline calculation of a number of lesions and a volume of all lesions identified for each subject.

Figure 6A:
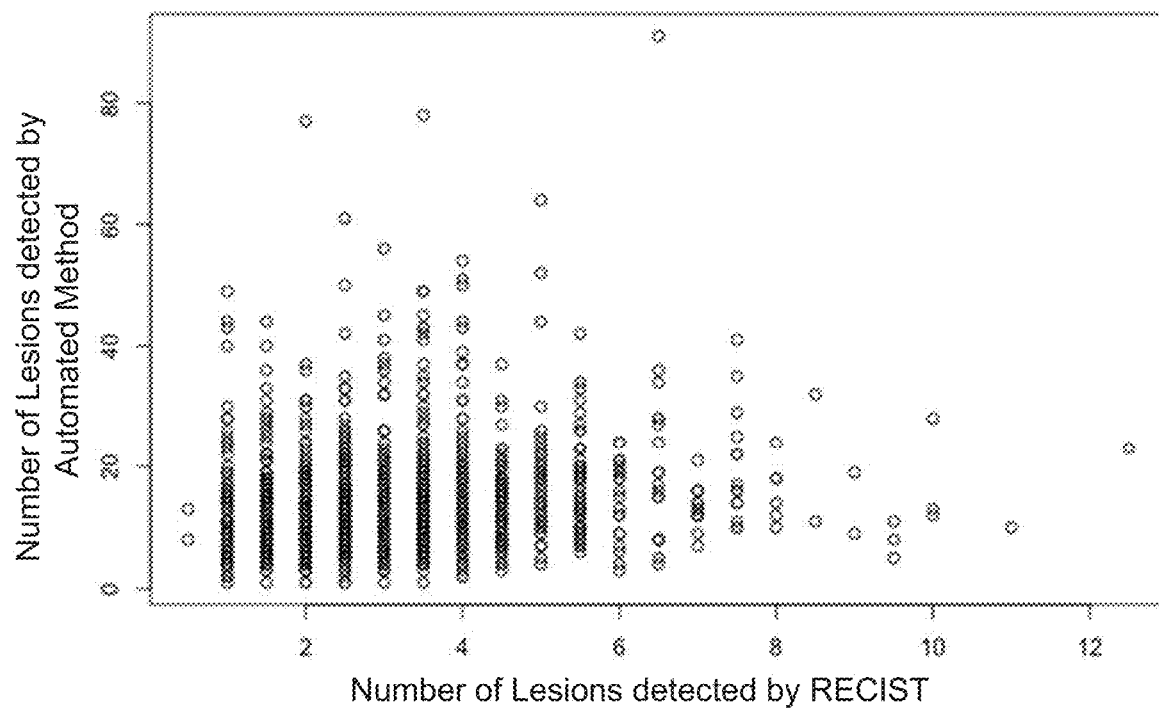
FIGS. 6A-6B illustrate plots comparing manual assessment using RECIST to the automated method for an exemplary training set. Panel A: comparisons for a number of identified lesions, Panel B: comparisons for determined sum of longest diameter (SLD).
Figure 6B:
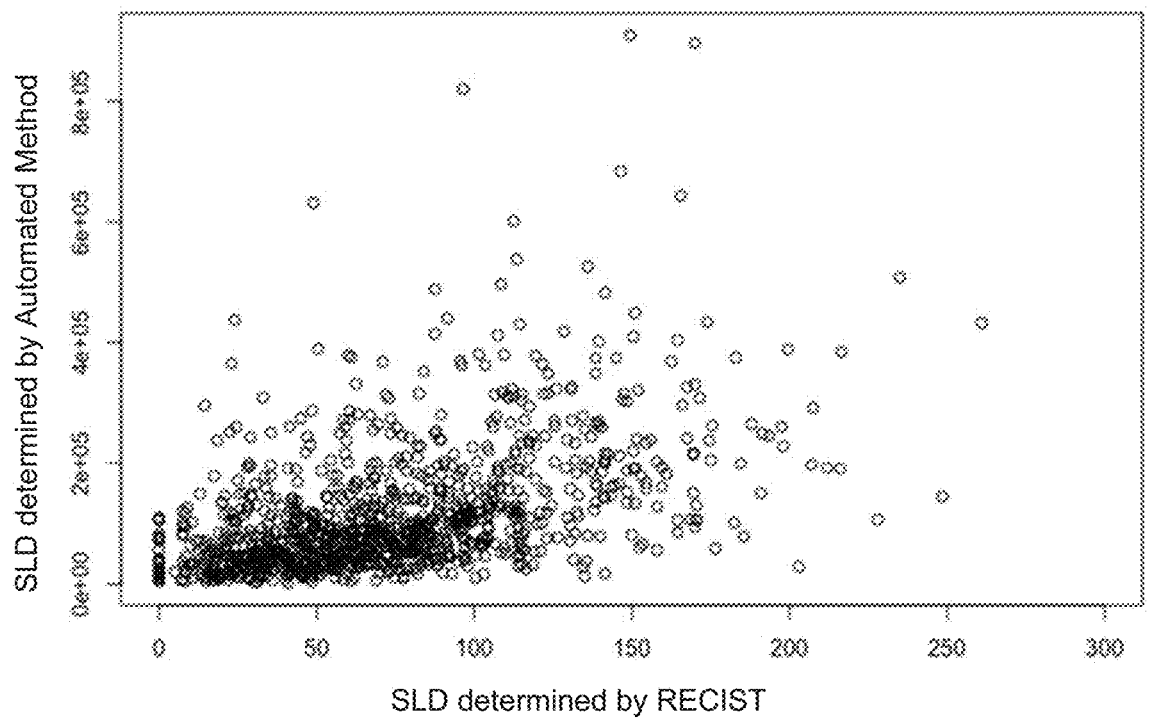
Figure 7A:
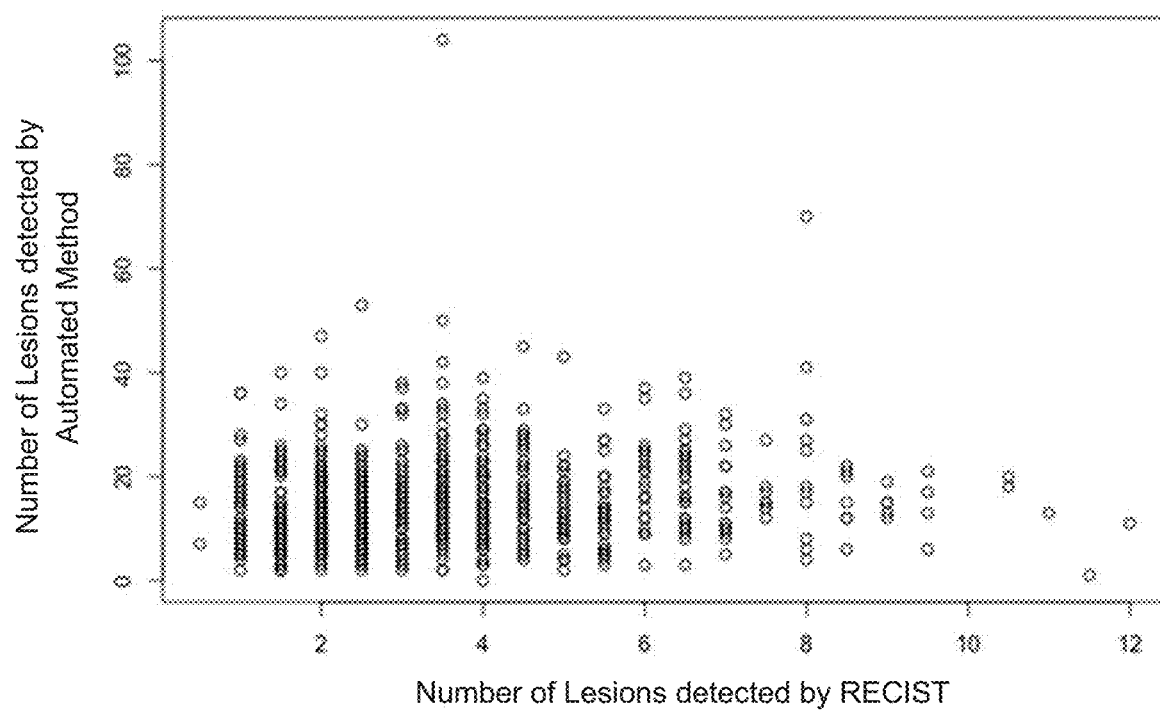
FIGS. 7A-7B illustrate plots comparing manual assessment using RECIST to the automated method for an exemplary test set. Panel A: comparisons for a number of identified lesions, Panel B: comparisons for determined SLD.
Figure 7B:
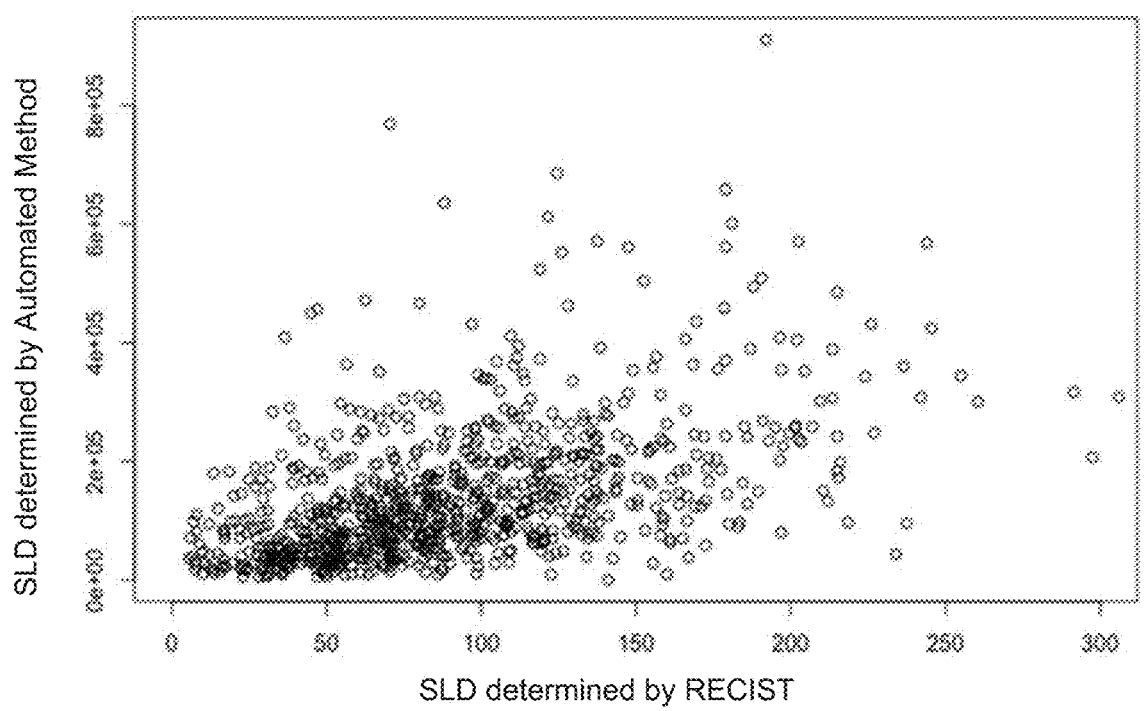

FIG. 6A shows a correlation plot comparing a number of lesions derived by RECIST reads (shown on the x-axis of the plot) and a number of lesions determined by the automated detection and segmentation method (shown on the y-axis) for the training data set (IMPower 150). FIG. 6B shows another plot comparing a tumor burden (e.g., measured as a total volume of all identified lesions) derived by RECIST (shown on the x-axis of the plot) and a tumor burden for the tumors identified by the automated method (shown on the y-axis of the plot). Both plots depict a rightward-skew, which illustrates that the RECIST reads had the highest correlation with the data from the automated method for lower ranges of the number of lesions and total volume of lesions. The standard deviation and standard error calculated based on differences between the two techniques' predictions of the number of lesions were 2.95 and 0.091, respectively. The standard deviation and standard error calculated based on differences between the two techniques' predictions of the total tumor volume were 5.2we+01 and 2.40, respectively. FIGS. 7A-7B depict similar correlation plots for the testing data set (IMPower131) with an average number of lesions determined using RECIST reads depicted on the x-axis and a number of lesions determined using the automated method depicted on the y-axis. With regard to the testing data set, the standard deviation and standard error calculated based on differences between the two techniques' predictions of the number of lesions were 6.05 and 0.24, respectively; and the standard deviation and standard error calculated based on differences between the two techniques' predictions of total lesion volume were 5.22e+01 with a standard error of 2.40, respectively.

Figure 8:
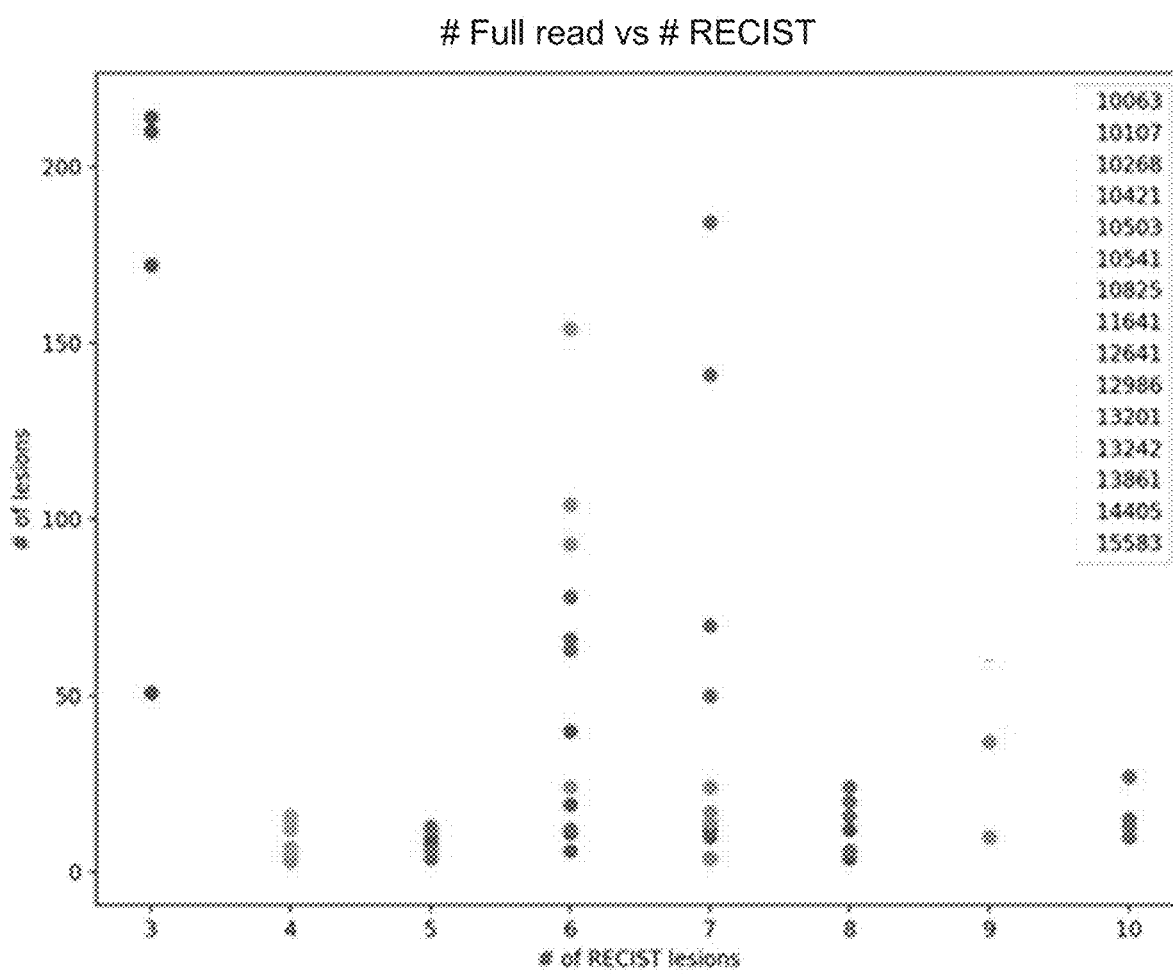
FIG. 8 illustrates a plot comparing a number of lesions identified using a full read performed by a radiologist to a number of lesions identified using the automated method for an exemplary training set.

The training data set (IMPower150) was further used in order to perform full reads, which involve determining an entire tumor burden for a subject via manual annotations of each tumor by a radiologist, rather than annotating only a single slice as performed in RECIST reads. FIG. 8 depicts a plot where the y-axis corresponds to a number of lesions determined by a radiologist (e.g., for a full read) and the x-axis corresponds to a number of lesions determined by RECIST for a set of subjects. Each point in the plot represents a subject within the training data set, for a total of 15 subjects that underwent both full reads and RECIST reads. The plot shows little agreement between RECIST and the full reads, as the full reads identify a greater amount of lesions compared to the RECIST reads. The standard deviation and standard error calculated based on differences between the two techniques' predictions was 6.64 and a standard error of 0.30.

Figure 9:
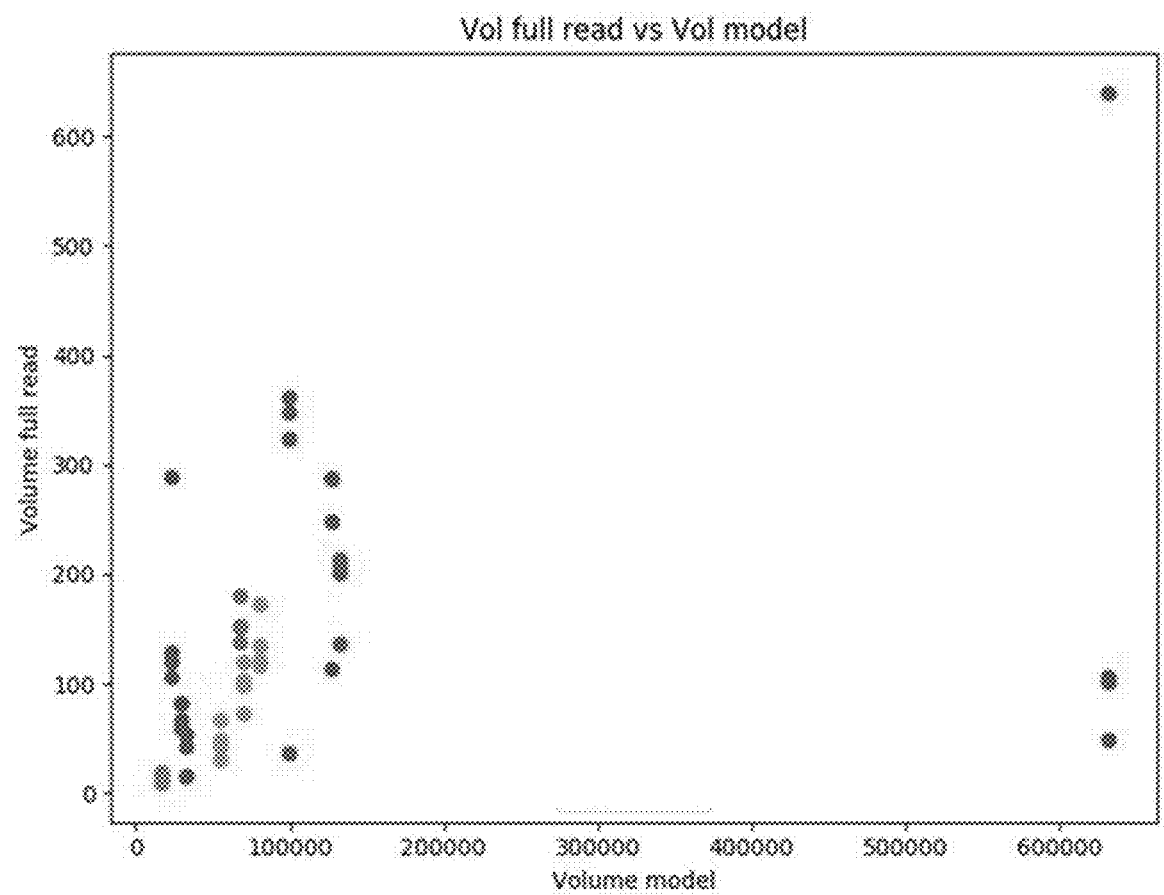
FIG. 9 illustrates a plot comparing a volume of lesions identified using full reads performed by one or more radiologists to a volume of lesions identified using the automated method for an exemplary training set.
Figure 10A:
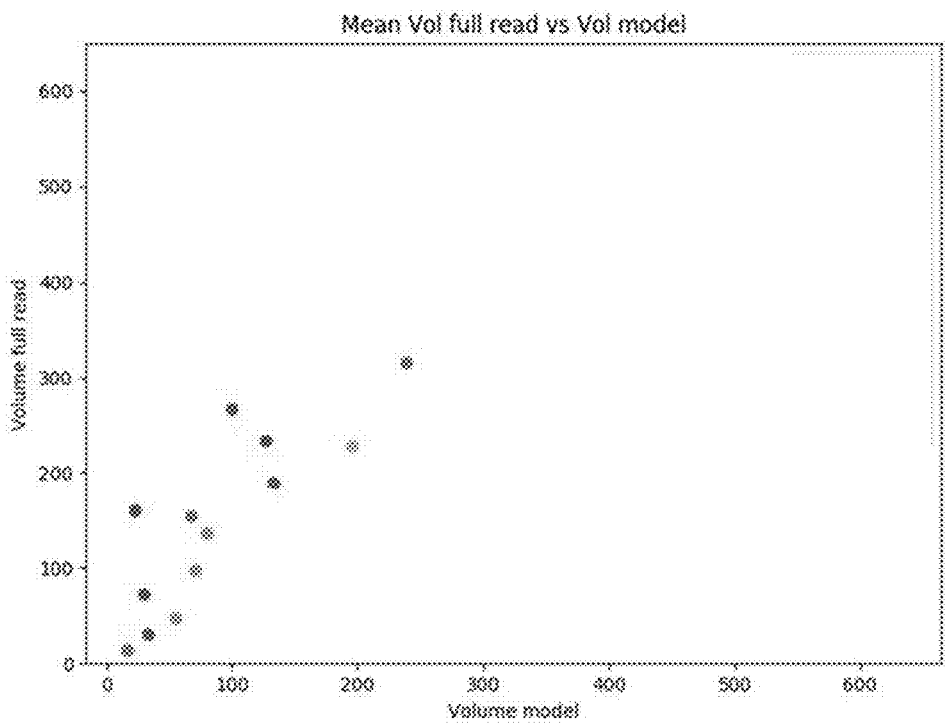
FIGS. 10A-10B illustrate plots comparing a mean and median volume of lesions identified using full reads to a volume of lesions identified using the automated method for an exemplary training set. Panel A: mean volume data. Panel B: median volume data.
Figure 10B:
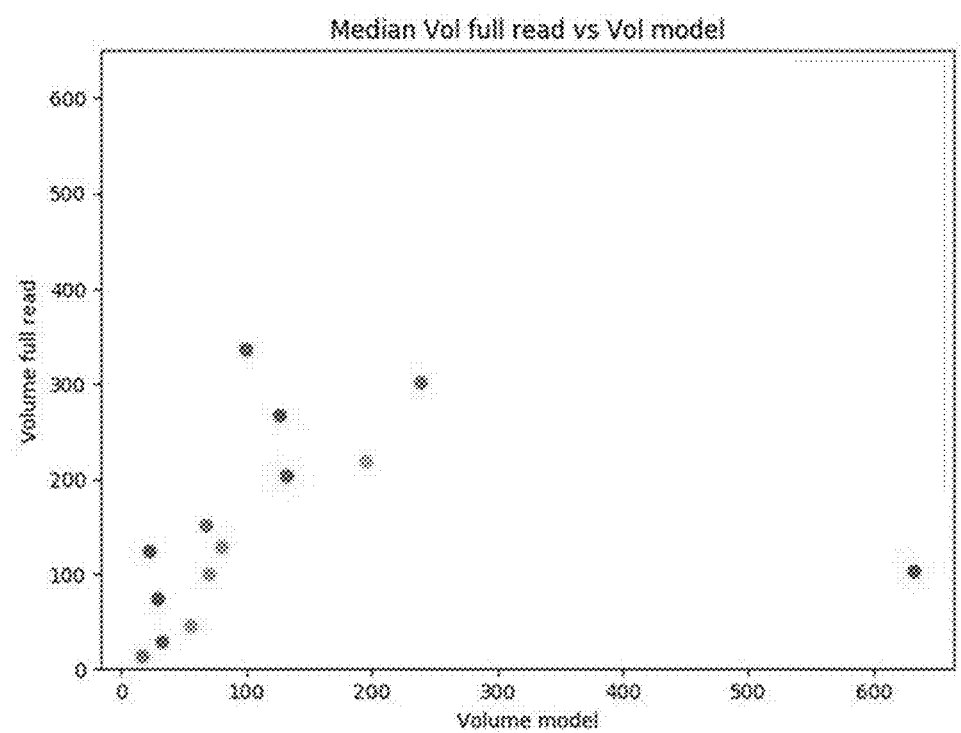

Further comparisons were also made between the automated method and full reads performed by a radiologist to determine an entire tumor burden for a subject. FIG. 9 depicts a correlation plot between a total lesion volume determined by a full read performed by a radiologist (shown on the y-axis) and a total lesion volume determined by the automated method (shown on the x-axis), such that each point represents a subject within the IMPower150 training data set. As shown in the plots, multiple reads were calculated for each subject from a set of training subjects. FIGS. 10A-10B show plots comparing a mean and median total lesion volume determined by the automated method (shown on the x-axes, respectively) and a mean and median total lesion volume determined by a full read for each subject (shown on the y-axes, respectively). Similar to FIGS. 8-9, each point in both of the plots represent a subject within the training data set. As depicted in the plots, the automated method generally identified a same or greater volume of lesions than the full reads.

Prognosis data was also collected for subjects represented in the training and testing data sets, such that a number of identified lesions and a calculated total volume of lesions were used to predict a probability of survival for subjects over a given time period. More specifically, subjects in the training data set were assigned to particular clusters based on various statistics of lesions detected using the RECIST technique, and a survival curve was calculated for each cluster to demonstrate whether various statistics were predictive of survival. FIGS. 11A-14B show Kaplan-Meier curves depicting exemplary prognosis data for the training data set.

Figures 11A, 11B:
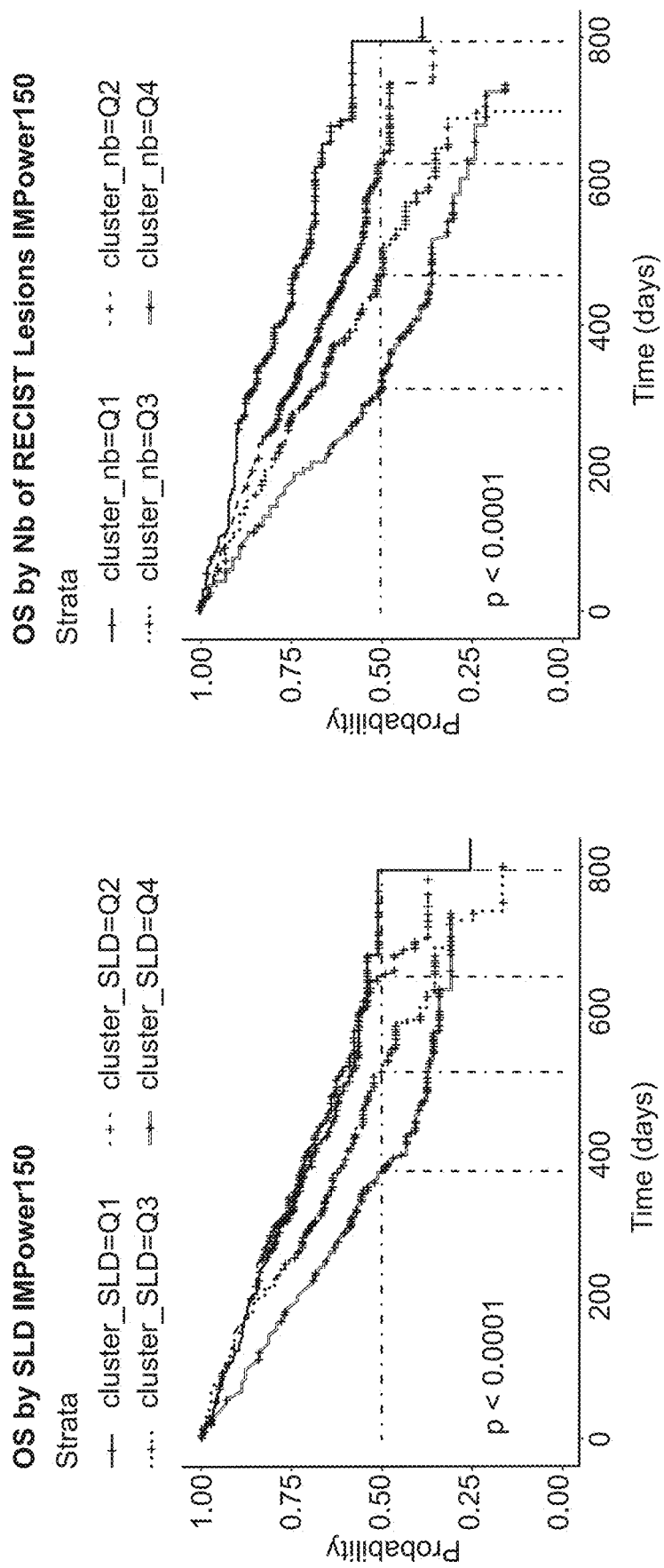
FIGS. 11A-11C illustrate Kaplan-Meier curves for an exemplary training set. Panel A: SLD derived by manually assessed RECIST, split into quartiles based on the derived SLD, Panel B: a number of lesions derived by manually assessed RECIST, split into quartiles based on the number of lesions. Panel C: Total SLD derived by the automated method, split into quartiles based on the derived total SLD.

FIG. 11A illustrates a probability of survival for subjects that have been clustered based on a SLD calculation for lesions identified by RECIST. FIG. 11B illustrates a probability of survival for subjects that have been clustered based on a number of lesions identified by RECIST. Y-axes of the plots correspond to the probability of survival and the x-axes correspond to an elapsed time period (e.g., measured in days). Clusters were determined such that a first quartile (Q1) corresponds to subjects with a number of lesions and/or a SLD score in the top 25%, a second quartile (Q2) corresponds to subjects within the next 25%, a third quartile (Q3) corresponds to subjects within the following 25%, and a fourth quartile (Q4) corresponds to subjects within the bottom 25%. As shown in the plots, subjects within the first quartile of the diameter sum SLD and subjects within the first quartile of the number of lesions have a lower probability of survival compared to subjects within the fourth quartile. Thus, the spatial statistics of automatically detected lesions appear to be predictive of survival prognosis.

Figure 11C:
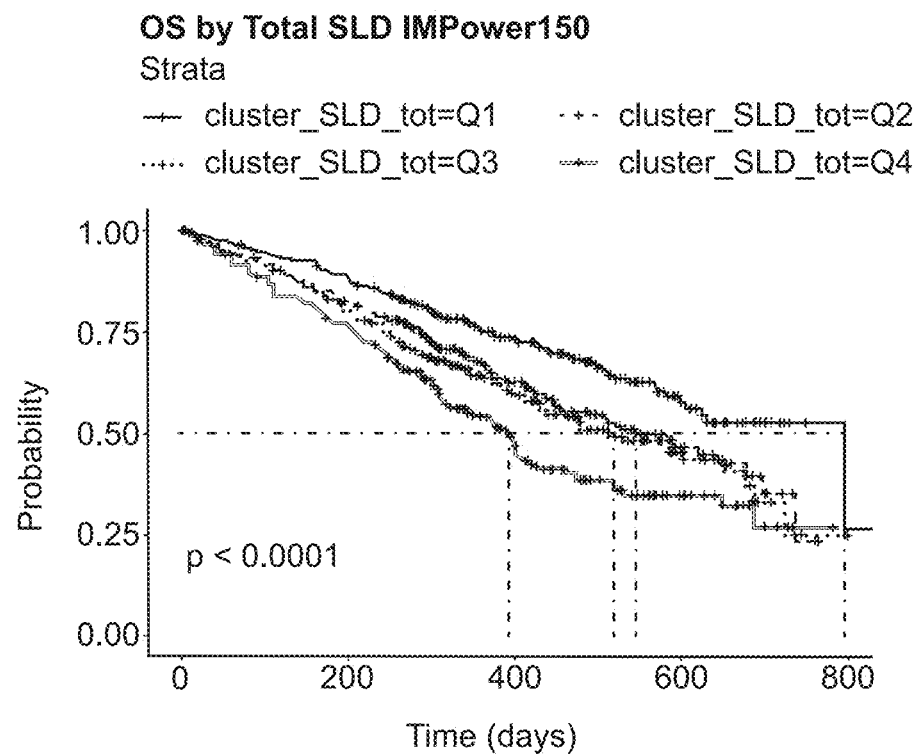
Figures 12A, 12B:
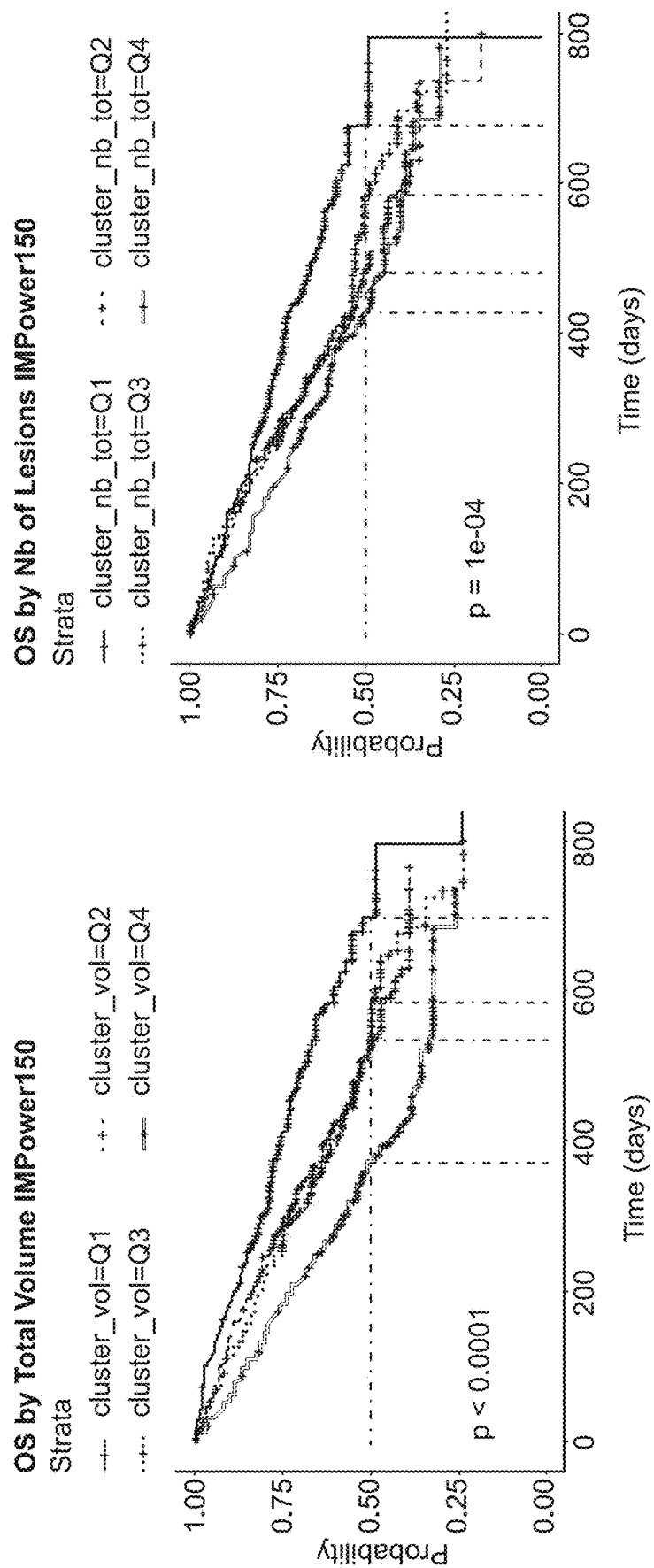
FIGS. 12A-12B illustrate Kaplan-Meier curves for an exemplary training set. Panel A: a total volume derived by the automated method, split by quartiles, Panel B: a number of lesions derived by the automated method, split by quartiles.

FIG. 11C instead shows a Kaplan-Meier curve that illustrates a probability of survival for subjects as determined from the disclosed automated method. FIG. 11C shows a plot depicting a probability of survival for subjects over a period of time, as determined by the automated method. With regard to the clustering associated with FIG. 11C, the subjects were clustered based on a total SLD for an entire tumor burden. FIGS. 12A-12B further depict plots for probability of survival for subjects based on a total volume and a number of identified lesions as also determined by the automated method. It is evident that a high tumor burden, measured by either a high volume of lesions or a high number of lesions, is correlated to lower probabilities of survival for subjects.

Figures 13A, 13B:
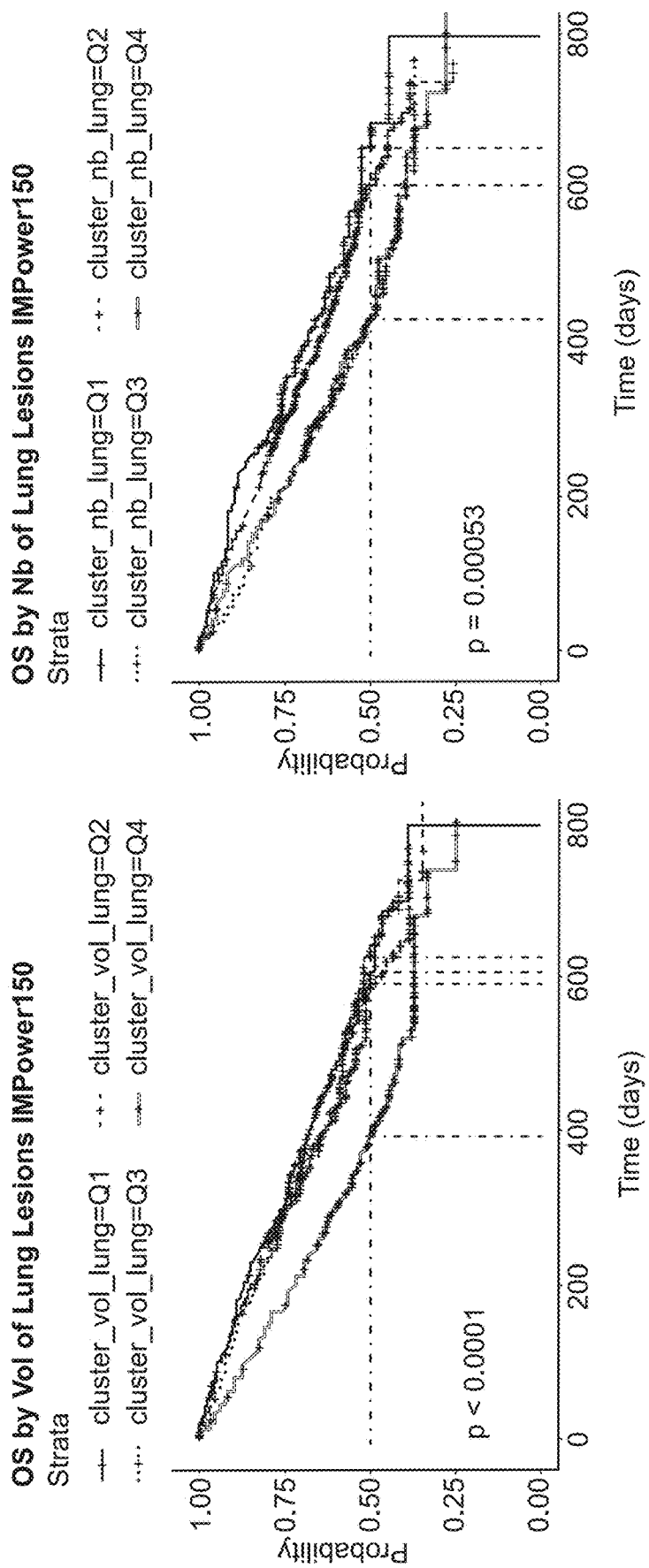
FIGS. 13A-13B illustrate Kaplan-Meier curves using lesions located within a lung region for an exemplary training set. Panel A: a volume of lung lesions derived by the automated method, split by quartiles, Panel B: a number of lung lesions derived by the automated method, split by quartiles.
Figure 14A:
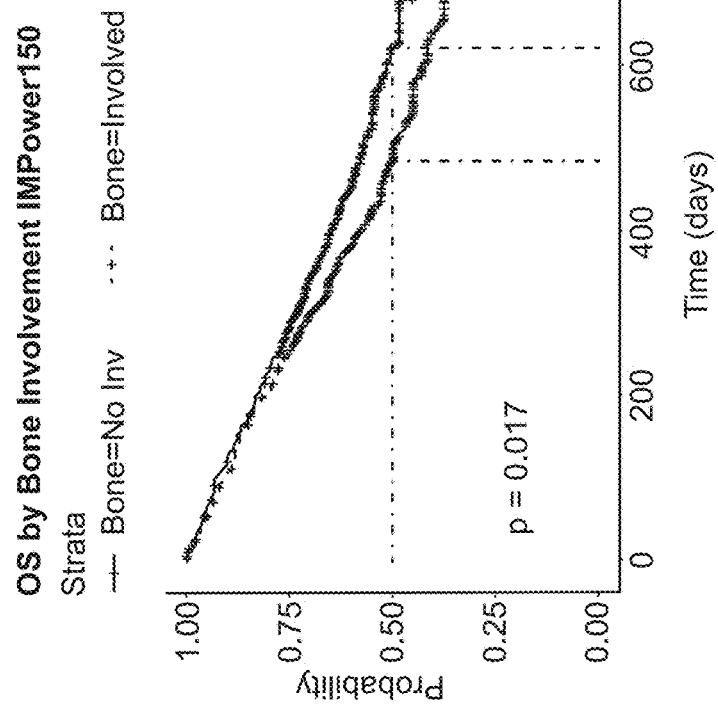
FIGS. 14A-14B illustrate Kaplan-Meier curves for an exemplary training set. Panel A: a measure of liver involvement derived by the automated method, split by quartiles, Panel B: a measure of bone involvement derived by the automated method, split by quartiles.
Figure 14B:
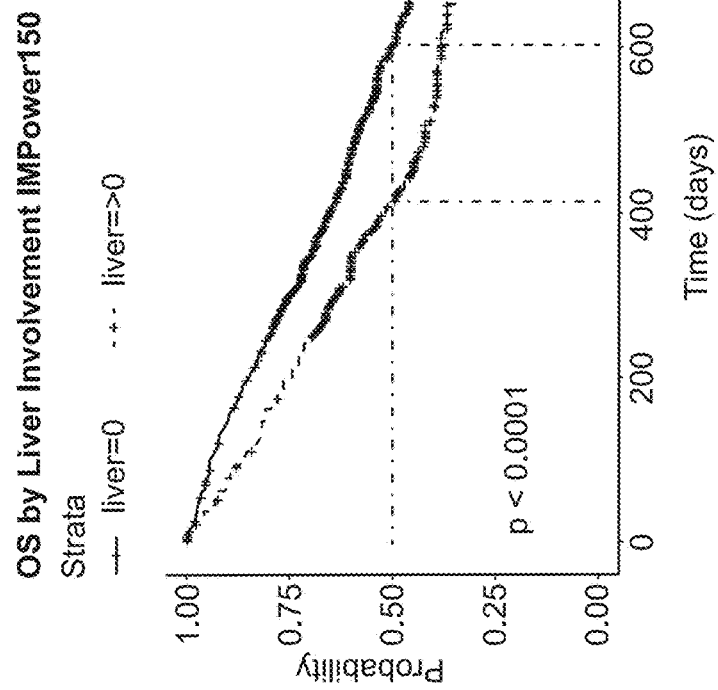
Figures 15A, 15B:
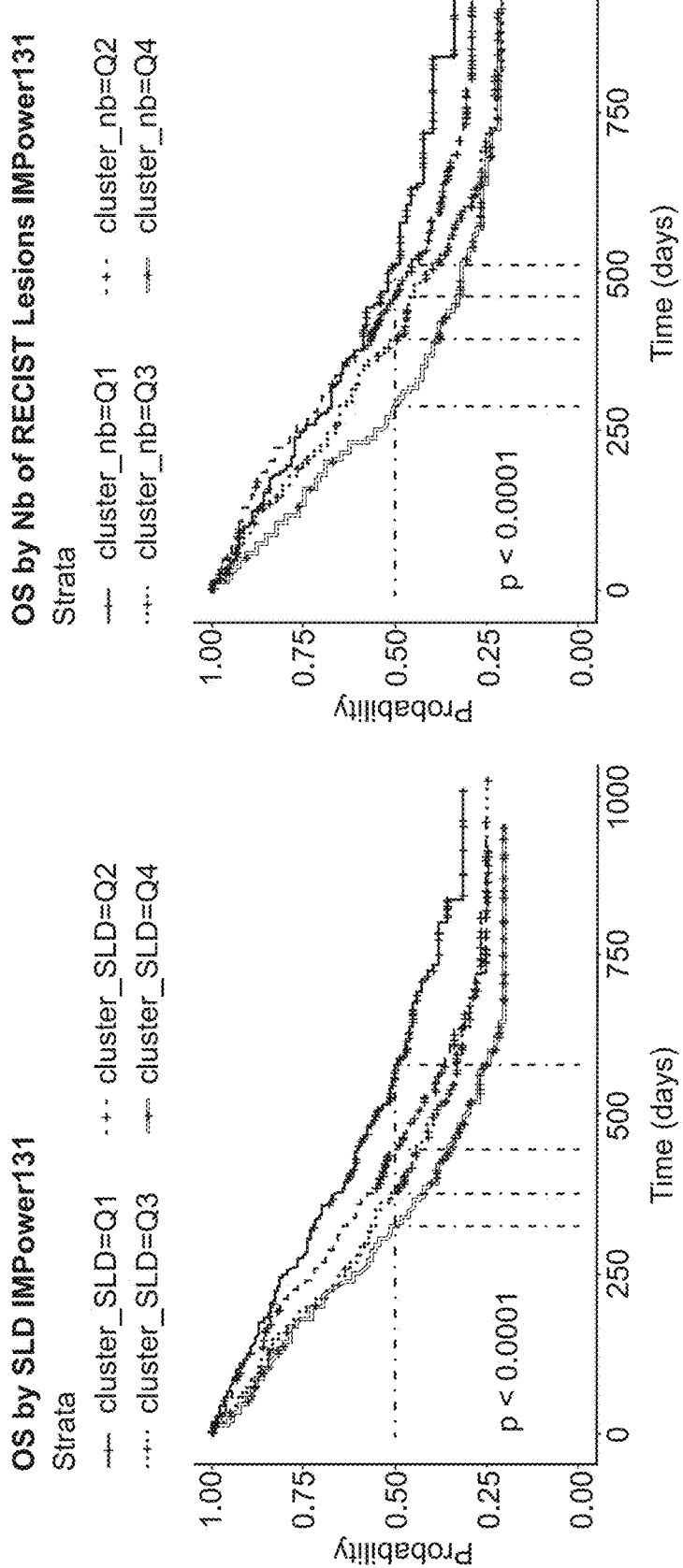
FIGS. 15A-15B illustrate Kaplan-Meier curves for an exemplary validation set. Panel A: SLD derived by manually assessed RECIST, split by quartiles, Panel B: a number of lesions derived by manually assessed RECIST, split by quartiles.
Figures 16A, 16B:
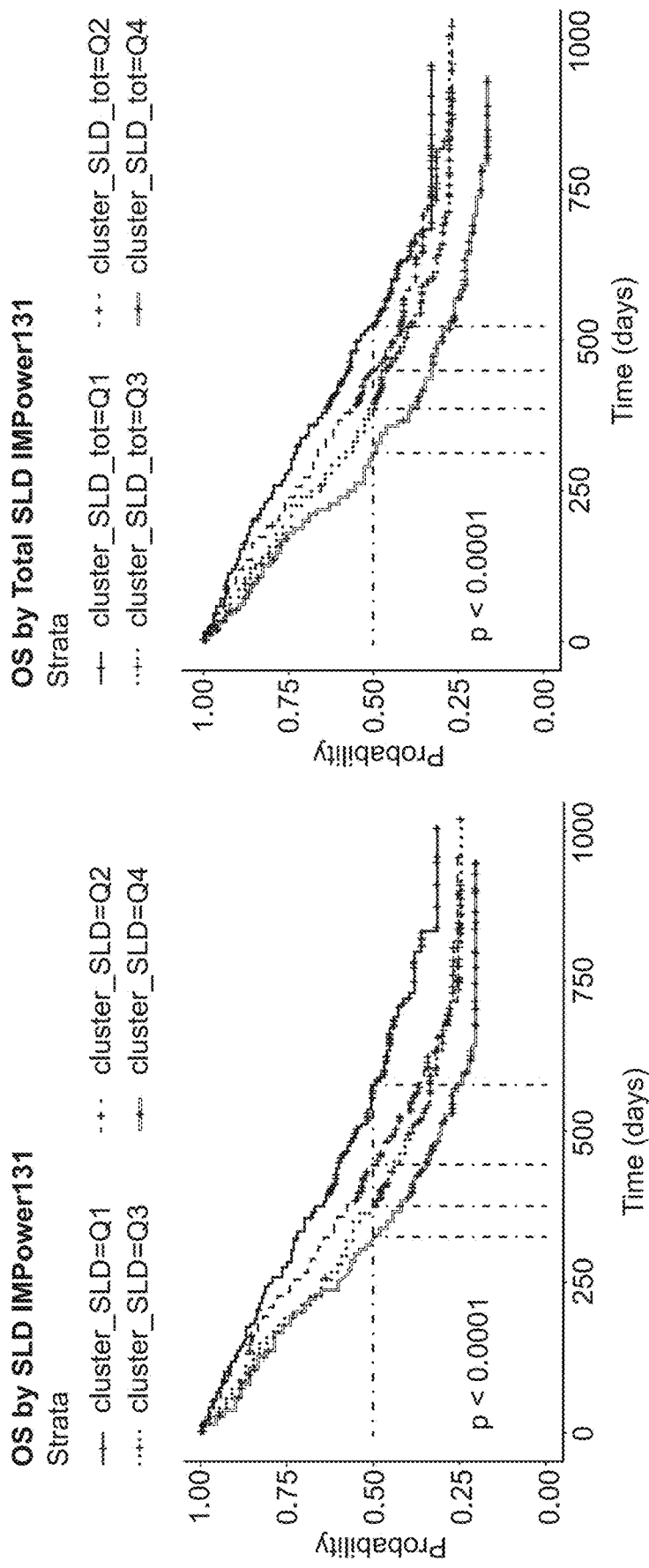
FIGS. 16A-16C illustrate Kaplan-Meier curves for an exemplary validation set. Panel A: SLD derived by manually assessed RECIST, split by quartiles, Panel B: Total SLD derived by the automated method, split by quartiles, Panel C: Total volume derived by the automated method, split by quartiles.
Figure 16C:
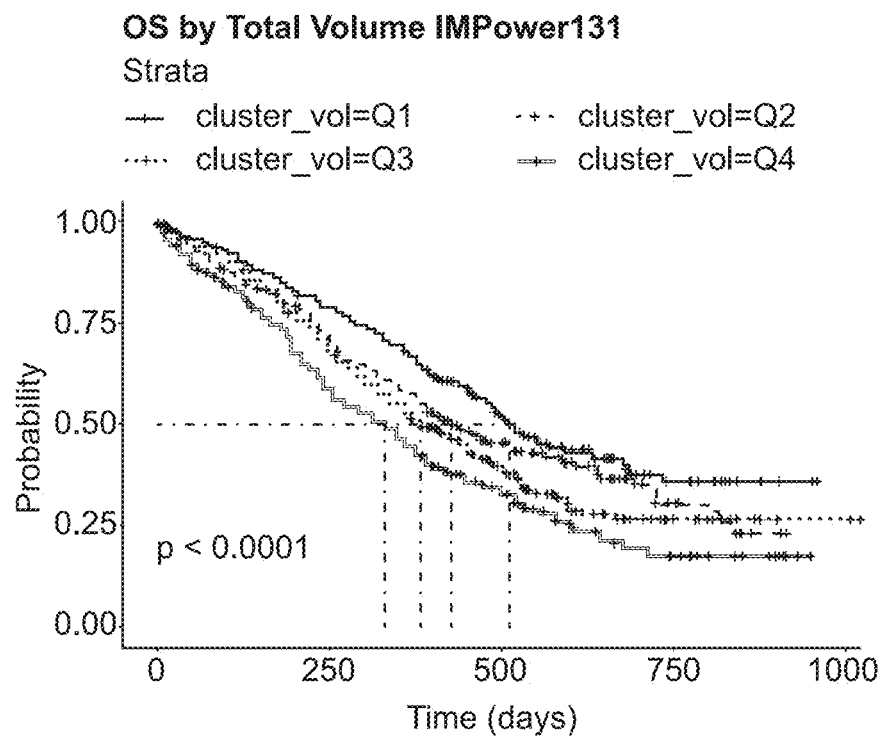
Figures 17A, 17B:
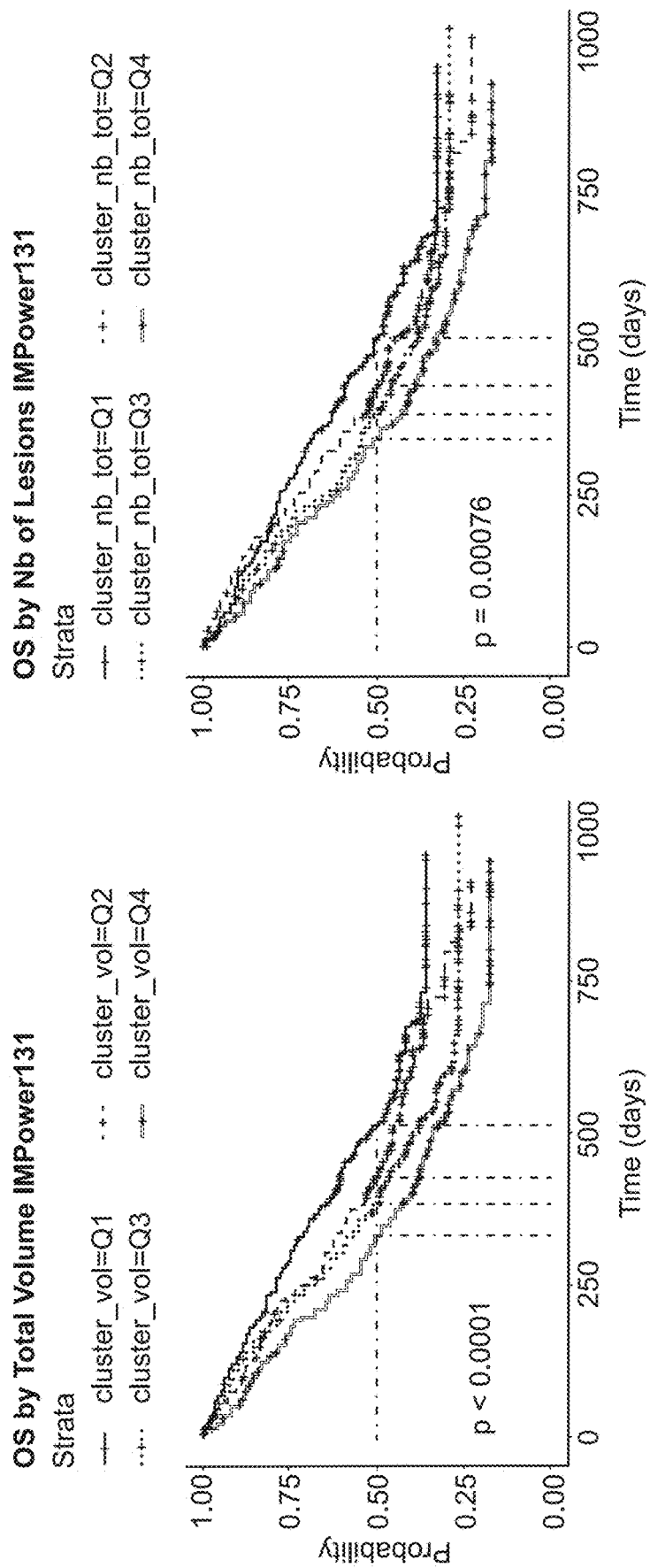
FIGS. 17A-17B illustrate Kaplan-Meier curves for an exemplary validation set. Panel A: a total tumor volume derived by the automated method, split by quartiles, Panel B: a number of lesions derived by the automated method, split by quartiles.
Figure 18A:
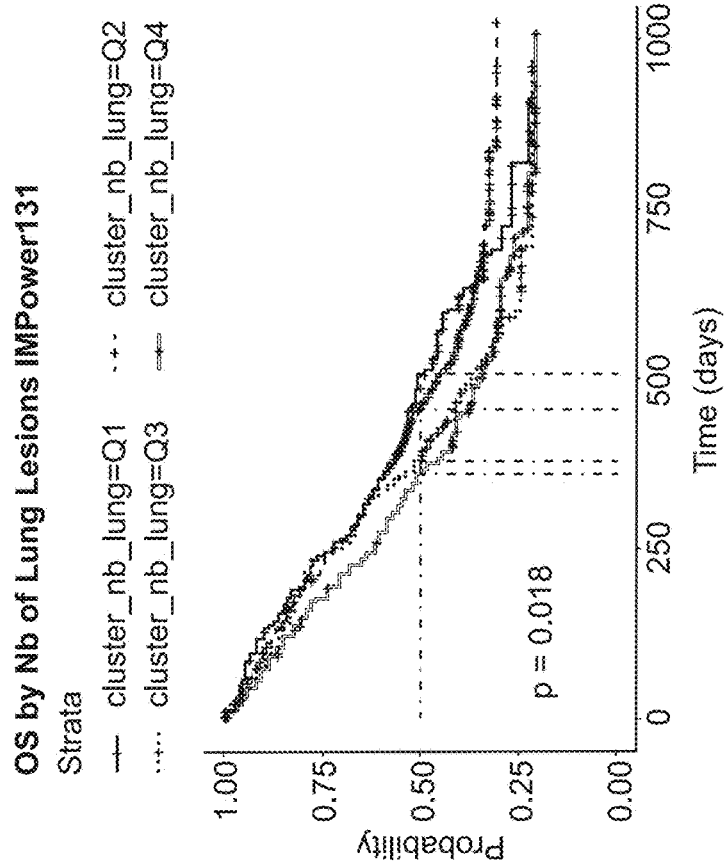
FIGS. 18A-18B illustrate Kaplan-Meier curves using lesions located within a lung region for an exemplary validation set. Panel A: a volume of lung lesions derived by the automated method, split by quartiles, Panel B: a number of lung lesions derived by the automated method, split by quartiles.
Figure 18B:
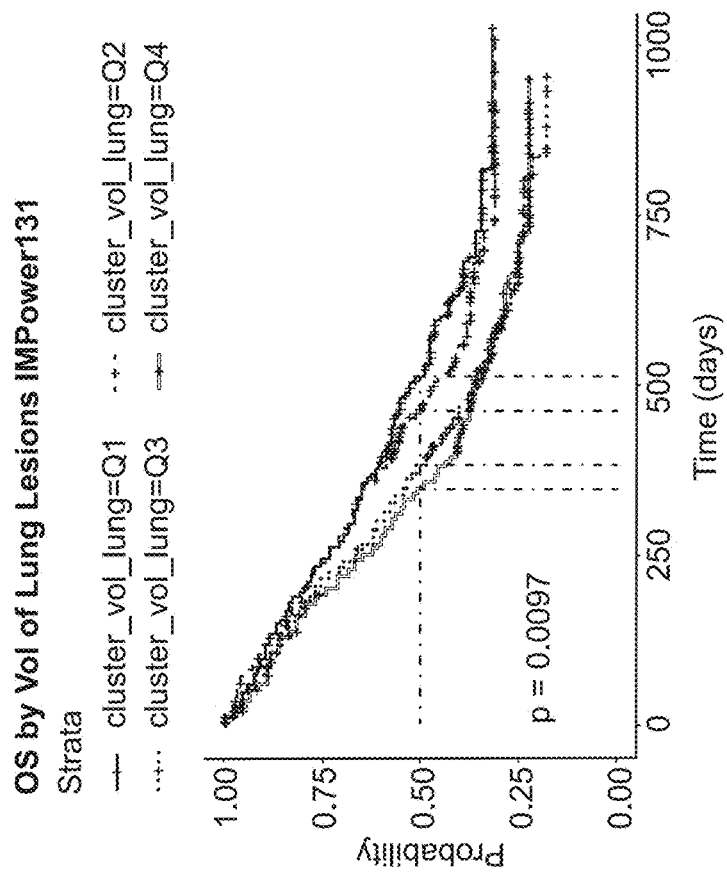

Identified locations of lesions were also used to assess a degree to which a prognosis (e.g., probability of survival) was predicted by statistics based on automated tumor detection and segmentation for subjects within the training data set as depicted in FIGS. 13A-14B. Specifically, FIGS. 13A-13B show a set of Kaplan-Meier curves depicting survival percentages for subjects. Subject groups were defined based on a volume of lung lesions (shown in the corresponding A plots) and a number of lung lesions (shown in the corresponding B plots). Notably, survival curves differed across subject groups, suggesting that lesion volume and lesion number were predictive of survival metrics. FIGS. 14A-14B shows a survival percentages for subjects based on the spread of lesions (e.g., metastasis) to lung and bone regions of a subject, respectively. Survival percentages were reported as higher when lesions were not present within either the lung or bone regions for a subject.

Figure 19:
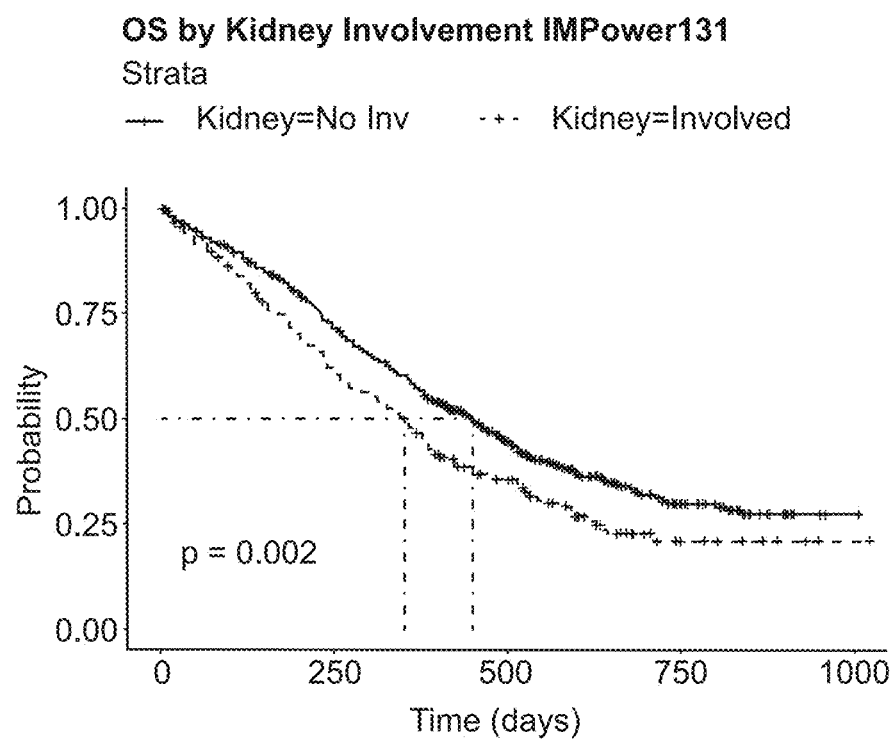
FIG. 19 illustrates a Kaplan-Meier curve for a measure of kidney involvement derived by the automated method for an exemplary validation set. Data for kidney involvement was split by quartiles.

FIGS. 15A-19 similarly depict Kaplan-Meier curves for exemplary prognosis data pertaining to the testing data set. FIGS. 15, 16, 17, and 18 correspond to same label variables (e.g., a y-axis corresponding to a probability of survival and a x-axis corresponding to an elapsed number of days) and methods as FIGS. 10, 11, 12, and 13, respectively. FIG. 19 shows a probability of survival for subjects based on the metastasis of a kidney region for subjects in the test data set.

It will be appreciated that the testing data set included different images from a different set of subjects than a training data set and was used to externally validate the results derived from hold-out portions of the training data set. In particular, the plots depicted in FIGS. 15A-19 depict prognoses for subjects that show greater correlations between a rate of survival and a location(s) and/or total amount or volume of tumors when determined by the automated method in comparison to RECIST or full reads.

VI.B. Implementation 2

VI.B.1. Overview

This Implementation uses the automated method of bounding-box detection and tumor segmentation to identify a full three-dimensional tumor burden on whole body diagnostic CT scans in subjects with advanced metastatic disease (i.e. lesions spread across multiple organs). The method differs from Implementation 1 in that organ-specific segmentation was not used to identify locations of the segmented tumors or generate organ masks.

The implemented method was based on the bounding-box detection network implemented as a RetinaNet for detection and tagging of lesions, followed by the tumorsegmentation network implemented as an ensemble of Probabilistic UNets enabling a segmentation of the detected lesions.

The presented work was developed using 2 multi-site clinical trials with over 84,000 identified RECIST lesions from 2,171 advanced Non-Small Cell Lung Cancer subjects across 364 clinical sites. As a result, the method accounted for inter-reader variability and heterogeneity of scan acquisitions across hospital sites. Tumors identified using the automated bounding-box detection and tumors segmentation techniques described in this disclosure were compared to manually identified RECIST tumors and manually segmented target lesions at the voxel level. In addition, the fully automatic estimates of baseline tumor burden were compared to radiologists' manual measurements with regard to the prognostic value of tumor burden for subjects' overall survival.

Results indicate state-of-the-art detection and segmentation performance for the RECIST target lesions on a hold-out set of 969 subjects, comprising over 35,000 tumors. Further, the results indicate that whole body tumor burden may have clinical utility as a prognostic factor of subject's overall survival time. The proposed method may be used to streamline tumor assessments in diagnostic radiology workflows, and if further developed, may potentially enable radiologists to assess response to therapy when applied sequentially.

VI.B.2. Methods

Techniques described in the present disclosure were used to identify a total tumor burden from Whole Body CT scans. The approach included three steps: bounding-box detection, tumor segmentation, and post-processing, and the resulting end-to-end method captured the varied nature of the available CT data and RECIST annotations.

The detection step utilized a bounding-box detection network, implemented as a RetinaNet, and identified both target- and non-target lesions using bounding boxes and lesion tags. RetinaNet uses a single-stage detection approach that provides for very fast object detection. Given that Whole Body CT scans often contain more than 200 axial slices, efficient processing was highly advantageous.

In the segmentation step, based only on the 2D segmentations of the target lesions, a tumor segmentation network, implemented as a set of probabilistic UNets, produced an ensemble of plausible axial lesion segmentations.

Tumor segmentation for metastatic cancer subjects is prone to reader subjectivity and thus there may not be a single ground truth for a given lesion. Probabilistic UNet [8] enables a memory efficient generative segmentation that allows to sample segmentation variants from a low-dimensional latent space. Use of probabilistic UNet for segmentation is further described at Kohl, S., et al. "A probabilistic U-Net for segmentation of ambiguous images." *Advances in Neural Information Processing Systems* (*NIPS* 2018) pp. 6965-6975 (2018), which is hereby incorporated by reference in its entirety for all purposes. The probabilistic UNet was thus selected mimic reader-to-reader annotation variability.

This part of the model allowed for the generation of ensembles that trade-off between inter-reader variability and overall agreement across radiologists' segmentations. The post-processing step joined the predicted 2D segmentations to produce unified whole-body 3D tumor masks. Further, post-processing also addressed the variability in image acquisition parameters (which led to different information limits and varying signal-to-noise ratios across scans) encountered in our multi-site dataset. Tumors detected via this automated technique were compared to those detected via a manual technique, where a radiologist outlined select target lesions and marked bounding boxes around non-target lesions.

VI.B.2.a. Tumor Detection

In the data assessed in this Implementation, tumor location tags were highly imbalanced across organs with lung lesions representing 45% and 40% of the training- and test data sets, respectively, but for which 128 locations accounted for less than 0.5% of tags. Focal loss was used to deal with the class imbalance.

A RetinaNet with a ResNet-50-FPN was used to detect tumors axially. (See Lin, T. Y., Dollar, P., Girshick, R., He, K., Hariharan, B., Belongie, S. "Feature pyramid networks for object detection." CVPR (2017), which is hereby incorporated by reference in its entirety for all purposes.) The maximum number of objects per image was set to 32 in the non-maximum suppression and the number of anchors to 9. Here, 32 represents an upper bound for the number of tumors that may reasonably be expected within a single axial slice. To provide spatial context around the central slice, the model was configured to receive as input three axial slices fed as three feature channels. Due to the low prevalence of many tags, classes were simplified to lungs, liver, bones, mediastinum and other locations.

In the test setting, the RetinaNet was applied sequentially to all axial slices. The predicted bounding boxes were expanded to the previous- and next slices to minimize false negatives.

VI.B.2.b. Tumor Segmentation

Experiments were conducted with $\beta=2$; 5; 10, either standalone or with intersection or union ensembling. The best results were obtained using the union of the 2 masks with $\beta=2$ and $\beta=10$.

Varying $\beta$ in the training loss allowed provision of different weights to the Kullback-Leibler divergence term in the loss, and hence giving different importance to spanning the latent space of segmentation variants. This parameter allowed the generation of tumor segmentation variants that mimic human reader variability or the generation of consensus segmentations.

A training dataset was constructed using RECIST target lesions segmentations from 2 radiologists per scan and 3D segmentation for some scans. The images were resampled to 0.7×0.7 mm in-plane resolution and patches of 256×256×3 pixels were constructed around these lesions. The previous and next slices were used as spatial context. Larger patches than the input were adopted, 180×180 pixels of 0.5×0.5 mm in-plane resolution. This selection was made, as the data to be assessed represented advanced-stage cancers, where the data depicts many large lesions.

Figure 20:
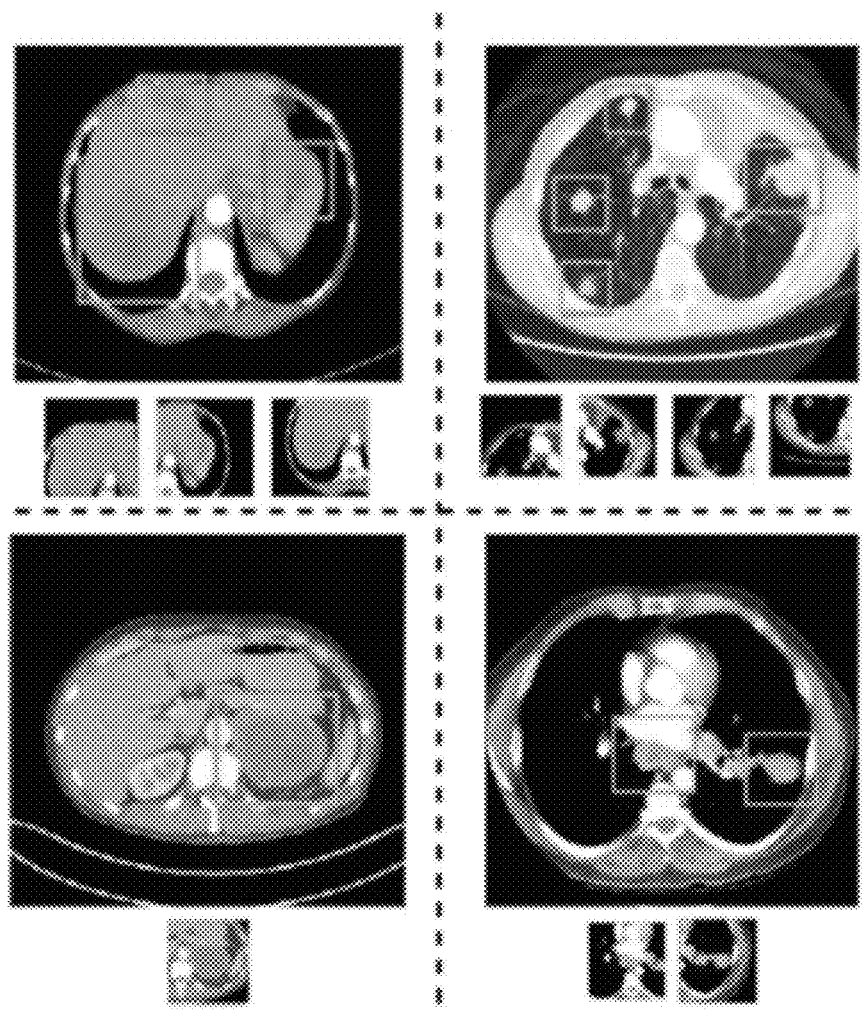
FIG. 20 shows examples of tumor detection and segmentation from axial CT scans using the automated detection and segmentation method. The top left panel shows three lesions detected in the liver, with the associated lesion segmentations in the plots below. Similarly, the top right panel shows four lesions detected in the lungs/mediastinum along with their associated segmentations. The two examples in the bottom panels show detected lesions in the kidney and lungs space, respectively.
Figure 21:
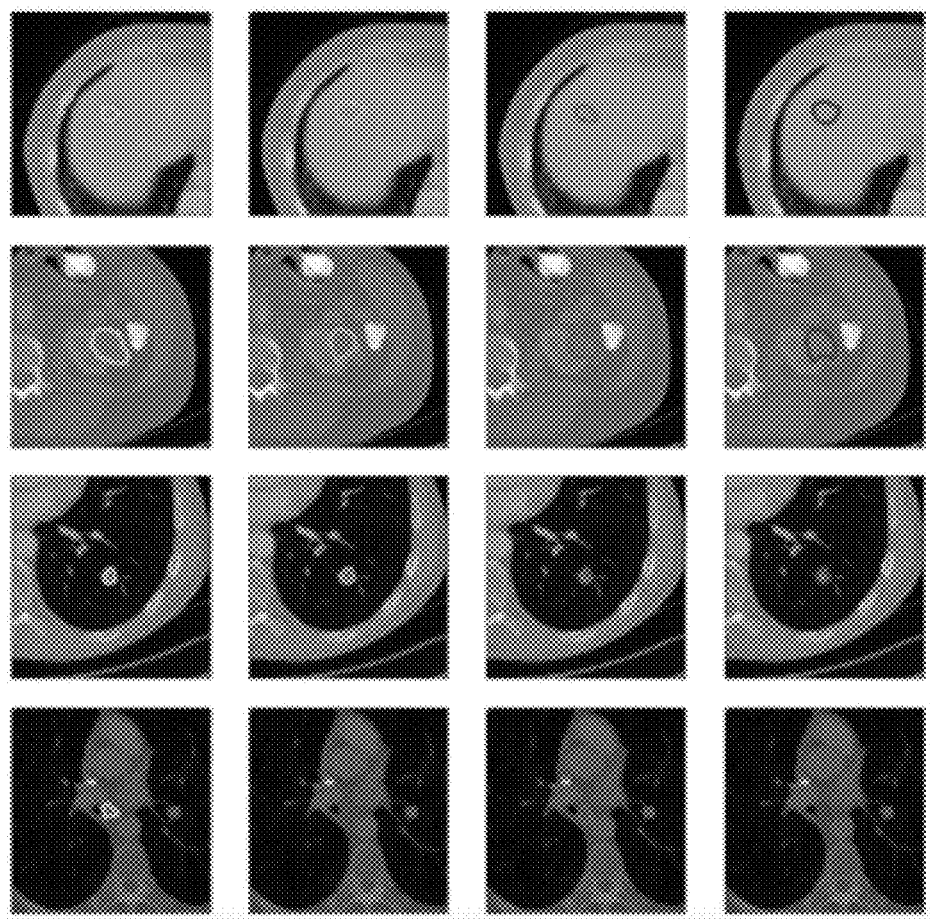
FIG. 21 illustrates examples of segmentation, from left to right per row: Radiologist annotations, Prob. UNet $\beta=10$, Prob. UNet $\beta=2$, union of the tumor segmentation network, implemented as a Probabilistic UNet.

In the test setting, patches centered on the detected lesions (for example, as provided by the detected bounding boxes) and were then resampled to the input resolution of the probabilistic UNets were segmented as shown in FIG. 20. When detected tumors were larger than the patch size, sliding windows were used to segment the totality of the detected tumor.

VI.B.2.c. Whole Body Assessment

Acquisition protocols vary from a hospital to another and from a machine to another even within same institution. As a result, the voxel size was variable in the dataset (from 0.6 to 1.45 mm in-plane and slice thickness ranging from 0.62 to 5 mm). These differences induced a variability in the Signal to Noise Ratio (SNR) and can lead to the segmentation of tumors that can only be detected on high resolution scans. To homogenize the information extracted from all CT scans, a binary closing was applied on the tumor masks using a cubic 3×3×5 mm structuring element to account for the difference in SNR and only keep tumors of height greater than 10 mm were kept.

VI.B.3. Experiment & Results

VI.B.3.a. Data

The dataset consisted of over 84k lesions from a total of 14,205 Diagnostic Computed Tomography scans from two randomized clinical trials. The training and test data were split per trial. A first trial (clinical trial NCT02366143, described in Socinski, M. A., et al. "Atezolizumab for First-Line Treatment of Metastatic Nonsquamous NSCLC." *N Engl J Med* 378, 2288-2301 (2018)) included 1,202 available advanced stage non-squamous Non-Small Cell Lung Cancer subjects. This first-trial dataset was used for training. A second trial (clinical trial NCT02367794) included 969 advanced stage squamous Non-Small Cell Lung Cancer subjects and was used as a hold-out set. The data was collected across 364 unique sites (238 in training set, 237 for test set), and a total of 27 different radiologists provided annotations. Thus, the data offers significant subject-, image acquisition-, and inter-reader variability.

For each trial, subjects had on average 6.5 visits for a total of 7861 scans in the training set and 6344 scans in the test set. Each scan was read by two radiologists according to RECIST 1.1 criteria. The tumor annotations consisted of 2D lesion segmentations for target lesions and bounding boxes for non-target lesions. In total, across all visits and radiologists, there were 48,470 annotated tumors in the training set and 35,247 in the test data. Further, for each identified target and non-target tumor, available lesion tags from 140 possible location labels were identified, as detailed in Table 1. In addition to the 2D annotations, 4,342 visits (2 visits per subject) resulted in volumetric segmentations for target tumors only. Whole body coverage was usable for full body assessments in 1,127 subjects at screening in the training set and for 914 subjects in the test set.

TABLE 1

Frequency of lesion locations in the training and test datasets. Sensitivity and accuracy.

| Location | Nr. Train(%) | Nr. Test(%) | Sensitivity |
| --- | --- | --- | --- |
| Lungs | 21843 (45%) | 14219 (40%) | 90.9 |
| Mediastinum | 10151 (21%) | 8566 (24%) | 87.4 |
| Liver | 2491 (5.1%) | 1926 (5.5%) | 92.3 |
| Bones | 1805 (3.7%) | 1204 (3.4%) | 87.8 |
| Other | 12180 (25%) | 9332 (26%) | 86.6 |
| Total | 48470 | 35247 | 87.9 |

VI.B.3.b. Results

Implementation. The RetinaNet for tumor detection and tagging was implemented using PyTorch and the ADAM optimizer. The ResNet-50-FPN was initialized using an ImageNet pretrained model. The learning rate was set 1e−4 and the batch size to 16. The network was trained for 416,000 iterations.

The Probabilistic UNets were implemented using PyTorch and the ADAM optimizer. The learning rate was set to 1e−5 and the batch size was set to 4. Two versions were retained with $\beta=2$ and 10 in the training loss. The networks were trained for 50 epochs.

Detection & Segmentation performance. The average lesion and class-level sensitivities per image for detection in Table 2 and Table 1. The sensitivities were obtained with an average of 0.89 "False positives" (FPs) per image. Due to the incompleteness of the RECIST annotations, these FPs may actually be non-annotated lesions. The average of the sensitivities were derived at 0.5, 1, 2 and 4 FPs per image (88.4%) as in Yan, K., et al.: MULAN: Multitask Universal Lesion Analysis Network for Joint Lesion Detection, Tagging, and Segmentation. In: Frangi, A. F., Schnabel, J. A., Davatzikos, C., Alberola-Lopez, C., Fichtinger, G. (eds.) MICCAI 2019. LNCS, vol. 11769, pp. 194-202. Springer, Cham (2019) and Liao, F., Liang, et. al.: Evaluate the malignancy of pulmonary nodules using the 3D deep leaky noisy-or network. IEEE Trans. Neural Netw. Learn. Syst. (2019).

TABLE 2

Accuracy and Segmentation Performances.

| Model | Detection | Segmentation sens. | Diam. Err.(mm)) |
| --- | --- | --- | --- |
| Tange et al. [4] | — | — | 1.7088 |
| MULAN[5] | 86.12 | — | 1.7837 |
| Ours | 87.9 | 78.2 | 1.6915 |

For segmentation, statistics included the average voxel-level sensitivity in the test set and the average error on the estimated longest dimensions of the RECIST lesions.

Prediction of Survival from Baseline Scans. Using the tumor detection and segmentation model estimated from the training data, lengths along the longest dimension on all detected and segmented lesions were calculated from the baseline scans of each subject in the test data set. With survival time as outcome variable, the right panel of FIG. 22 shows the Kaplan-Meier plot based on the empirical quartiles of the by-model extracted baseline SLD (for the subjects in the test set). For comparison, on the same subjects, the left panel shows the Kaplan-Meier plot based on empirical quartiles for SLD derived by RECIST. As can be seen, compared to that generated through radiologist annotations according to the RECIST criteria, the automated method largely reproduced the tumor burden pre-treatment survival risk profile.

VI.B.4. Interpretation

The results exemplify strong performance of the multi-stage segmentation platform. The fully automatic algorithm successfully identified and performed 3D segmentation of tumors on standard diagnostic whole body CT scans. The methodology demonstrated strong performance for detection and segmentation compared to a radiologist, and importantly, worked well for tumors in multiple different organs. These results indicate that the technique may be a powerful support tool for radiologists by providing initial tumor burden assessments for their review, which should improve accuracy, reproducibility and speed. In addition, the algorithm generated metrics such as full-body tumor volume (typically too time consuming for radiologists to assess), which may be valuable as a prognostic tool or novel endpoint for clinical trials, as well as providing a more complete view of a subjects' disease for use in clinical radiology practice.

VII. Additional Considerations

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the concepts herein disclosed may be resorted to by those skilled in the art, and that such modifications and variations are considered to be within the scope of this invention as defined by the appended claims.

The ensuing description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

What is claimed:

1. A computer-implemented method comprising:
    accessing one or more medical images of a subject;
    inputting the one or more medical images into a detection network to generate one or more masks that identifies a set of regions within the one or more medical images, wherein the detection network predicts that each region of the set of regions identified in the one or more masks includes a depiction of a tumor of one or more tumors within the subject;
    processing, for each region of the set of regions, the region of the one or more medical images using a tumor segmentation network to generate one or more tumor segmentation boundaries for the tumor present within the subject;
    determining, for each tumor of the one or more tumors and by using a plurality of organ-specific segmentation networks, an organ within which at least part of the tumor is located, wherein each organ-specific segmentation network of the plurality of organ-specific segmentation networks is a neural network; and
    generating an output based on the one or more tumor segmentation boundaries and locations of the organs within which at least part of the one or more tumors are located.

2. The method of claim 1, wherein processing the region to generate the one or more tumor segmentation boundaries includes:
    identifying, for each of multiple 2D medical image, a segmentation boundary of the tumor within a tumor segmentation boundary of the one or more tumor segmentation boundaries; and
    defining a three-dimensional segmentation boundary based on the segmentation boundaries associated with multiple 2D medical images, wherein the output includes or depicts the three-dimensional segmentation boundary.

3. The method of claim 1, wherein each of the one or more tumor segmentation boundaries is defined to be a segmentation perimeter of a two-dimensional cross section of the tumor depicted, wherein the output includes or depicts the one or more tumor segmentation boundaries.

4. The method of claim 1, further comprising:
    determining, for each tumor of the one or more tumors and based on a tumor segmentation boundary of the one or more tumor segmentation boundaries, a spatial attribute that includes:
        a volume of the tumor;
        a length of the tumor along a particular dimension or longest dimension; and/or
        a cross-sectional area of the tumor; and
    calculating, based on the spatial attributes, a subject-level tumor statistic of the one or more tumors, wherein the output includes the subject-level tumor statistic.

5. The method of claim 4, wherein the one or more tumors includes a plurality of tumors, wherein the spatial attribute determined for each tumor of the one or more tumors includes the length of the tumor along a longest dimension, and wherein the subject-level tumor statistic includes a sum of the lengths of the tumors.

6. The method of claim 1, further comprising:
    determining a percentage or absolute difference between the subject-level tumor statistic and another tumor statistic associated with the subject, the other tumor statistic having been generated based on an analysis of one or more other medical images of the subject, each of the one or more other medical images having been collected at a benchmark time prior to a time at which the one or more medical images were collected, wherein the output includes or is based on the percentage or absolute difference.

7. The method of claim 6, further comprising:
    comparing the percentage or absolute difference to each of one or more predetermined thresholds; and
    determining an estimate of a prognosis, of a treatment response or of a disease state based on the threshold comparison, wherein the output includes the estimated prognosis, treatment response or disease state.

8. The method of claim 1, wherein the one or more medical images includes one or more computed tomography (CT) images.

9. The method of claim 1, wherein the one or more medical images include a whole-body or torso CT image.

10. The method of claim 1, wherein the one or more medical images includes one or more MRI images.

11. The method of claim 1, wherein the detection network is configured to use focal loss.

12. The method of claim 1, wherein the tumor segmentation network includes a modified U-Net that includes separable convolutions.

13. The method of claim 1, wherein each of the plurality of organ-specific segmentation networks includes a modified U-Net that includes separable convolutions.

14. The method of claim 1, further comprising:
    determining, for each tumor of the one or more tumors and based on a being located within the organ, wherein the output includes the organ-specific counts.

15. The method of claim 1, further comprising:
capturing the one or more medical images with a CT machine.

16. A system comprising:
one or more data processors; and
a non-transitory computer readable storage medium containing instructions which, when executed on the one or more data processors, cause the one or more data processors to perform processing comprising:
  accessing one or more medical images of a subject;
  inputting the one or more medical images into a detection network to generate one or more masks that identifies a set of regions within the one or more medical images, wherein the detection network predicts that each region of the set of regions identified in the one or more masks includes a depiction of a tumor of one or more tumors within the subject;
  processing, for each region of the set of regions, the region of the one or more medical images using a tumor segmentation network to generate one or more tumor segmentation boundaries for the tumor present within the subject;
  determining, for each tumor of the one or more tumors and by using a plurality of organ-specific segmentation networks, an organ within which at least part of the tumor is located, wherein each organ-specific segmentation network of the plurality of organ-specific segmentation networks is a neural network; and
  generating an output based on the one or more tumor segmentation boundaries and locations of the organs within which at least part of the one or more tumors are located.

17. The system of claim 16, wherein processing the region to generate the one or more tumor segmentation boundaries includes:
  identifying, for each of multiple 2D medical image, a segmentation boundary of the tumor within a tumor segmentation boundary of the one or more tumor segmentation boundaries; and
  defining a three-dimensional segmentation boundary based on the segmentation boundaries associated with multiple 2D medical images, wherein the output includes or depicts the three-dimensional segmentation boundary.

18. The system of claim 16, wherein each of the one or more tumor segmentation boundaries is defined to be a segmentation perimeter of a two-dimensional cross section of the tumor depicted, wherein the output includes or depicts the one or more tumor segmentation boundaries.

19. A computer-program product tangibly embodied in a non-transitory machine-readable storage medium, including instructions configured to cause one or more data processors to perform processing comprising:
  accessing one or more medical images of a subject;
  inputting the one or more medical images into a detection network to generate one or more masks that identifies a set of regions within the one or more medical images, wherein the detection network predicts that each region of the set of regions identified in the one or more masks includes a depiction of a tumor of one or more tumors within the subject;
  processing, for each region of the set of regions, the region of the one or more medical images using a tumor segmentation network to generate one or more tumor segmentation boundaries for the tumor present within the subject;
  determining, for each tumor of the one or more tumors and by using a plurality of organ-specific segmentation networks, an organ within which at least part of the tumor is located, wherein each organ-specific segmentation network of the plurality of organ-specific segmentation networks is a neural network; and
  generating an output based on the one or more tumor segmentation boundaries and locations of the organs within which at least part of the one or more tumors are located.

20. The computer-program product of claim 19, wherein processing the region to generate the one or more tumor segmentation boundaries includes:
  identifying, for each of multiple 2D medical image, a segmentation boundary of the tumor within a tumor segmentation boundary of the one or more tumor segmentation boundaries; and
  defining a three-dimensional segmentation boundary based on the segmentation boundaries associated with multiple 2D medical images, wherein the output includes or depicts the three-dimensional segmentation boundary.

* * * * *